United States Patent
Levy

(10) Patent No.: US 12,073,933 B2
(45) Date of Patent: Aug. 27, 2024

(54) METHOD AND SYSTEM FOR REMOTELY IDENTIFYING AND MONITORING ANOMALIES IN THE PHYSICAL AND/OR PSYCHOLOGICAL STATE OF AN APPLICATION USER USING BASELINE PHYSICAL ACTIVITY DATA ASSOCIATED WITH THE USER

(71) Applicant: Mahana Therapeutics, Inc., San Francisco, CA (US)

(72) Inventor: Simon Levy, San Francisco, CA (US)

(73) Assignee: Mahana Therapeutics, Inc., San Francisco, CA (US)

( * ) Notice: Subject to any disclaimer, the term of this patent is extended or adjusted under 35 U.S.C. 154(b) by 406 days.

(21) Appl. No.: 16/888,061

(22) Filed: May 29, 2020

(65) Prior Publication Data
US 2021/0375423 A1 Dec. 2, 2021

(51) Int. Cl.
G16H 20/30 (2018.01)
A61B 5/00 (2006.01)
(Continued)

(52) U.S. Cl.
CPC ............ *G16H 20/30* (2018.01); *A61B 5/1113* (2013.01); *A61B 5/1123* (2013.01);
(Continued)

(58) Field of Classification Search
CPC ........ G16H 10/60; G16H 20/10; G16H 20/70; G16H 40/67; G16H 80/00; G16H 20/60;
(Continued)

(56) References Cited

U.S. PATENT DOCUMENTS 7,764,990 B2 * 7/2010 Martikka ............... A61B 5/389
607/48
9,467,789 B1 10/2016 Zhao et al.
(Continued)

FOREIGN PATENT DOCUMENTS

EP 3711666 9/2020
EP 3711666 A1 * 9/2020 ........... A61B 5/1038
(Continued)

OTHER PUBLICATIONS

Dang, et al. "Role of digital therapeutics and the changing future of healthcare," Journal of Family Medicine and Primary Care, May 31, 2020, vol. 9, issue 5, pp. 2207-2213.
(Continued)

*Primary Examiner* — Rufus C Point
(74) *Attorney, Agent, or Firm* — Hawley Troxell Ennis & Hawley LLP; Rivkah Young

(57) ABSTRACT

An application user is granted access to one or more applications that provide the user with information and assistance. Altitude and/or motion data is collected from one or more devices associated with the user, and the device altitude and/or motion data is utilized to identify physical activities being performed by the user. The device altitude and/or motion data is further analyzed to determine physical activity count data, physical activity speed, velocity, and/or acceleration data, and physical activity length data. The physical activity data is then analyzed to identify and monitor changes or anomalies in the physical and/or psychological state of the user using baseline physical activity data. Upon identification of changes or anomalies in the user's physical and/or psychological state, one or more actions are taken to assist the user.

22 Claims, 8 Drawing Sheets

(51) Int. Cl.
  *A61B 5/11* (2006.01)
  *G16H 10/60* (2018.01)
  *G16H 20/10* (2018.01)
  *G16H 20/70* (2018.01)
  *G16H 40/67* (2018.01)
  *G16H 80/00* (2018.01)

(52) U.S. Cl.
  CPC .......... *A61B 5/7275* (2013.01); *A61B 5/7435* (2013.01); *A61B 5/748* (2013.01); *G16H 10/60* (2018.01); *G16H 20/10* (2018.01); *G16H 20/70* (2018.01); *G16H 40/67* (2018.01); *G16H 80/00* (2018.01); *A61B 5/6898* (2013.01)

(58) Field of Classification Search
  CPC .... G16H 50/20; A61B 5/6898; A61B 5/6803; A61B 5/681; A61B 2562/0219; A61B 5/1116; A61B 5/1118; A61B 5/165; A61B 5/4836; A61B 5/7267
  See application file for complete search history.

(56) References Cited

U.S. PATENT DOCUMENTS

| | | | |
|---|---|---|---|
| 9,536,052 B2 | 1/2017 | Amarasingham et al. | |
| 9,642,573 B2 | 5/2017 | Zhao et al. | |
| 10,595,159 B1* | 3/2020 | Nelson | H04L 67/306 |
| 11,045,126 B2 | 6/2021 | Matic et al. | |
| 11,164,596 B2 | 11/2021 | Jain et al. | |
| 2003/0139946 A1 | 7/2003 | Van Mierlo et al. | |
| 2005/0065813 A1 | 3/2005 | Mishelevich et al. | |
| 2006/0079800 A1* | 4/2006 | Martikka | A61B 5/6804 |
| | | | 600/546 |
| 2006/0136173 A1* | 6/2006 | Case | G01C 22/006 |
| | | | 702/182 |
| 2007/0260641 A1 | 11/2007 | Bohannon et al. | |
| 2010/0169409 A1 | 7/2010 | Fallon et al. | |
| 2011/0077971 A1 | 3/2011 | Surwit et al. | |
| 2011/0119212 A1 | 5/2011 | De Bruin et al. | |
| 2011/0172059 A1 | 7/2011 | Watterson et al. | |
| 2011/0295843 A1* | 12/2011 | Ingrassia, Jr. | G06F 16/4387 |
| | | | 707/723 |
| 2012/0035021 A1 | 2/2012 | Saalasti et al. | |
| 2012/0083705 A1 | 4/2012 | Yuen et al. | |
| 2012/0150074 A1 | 6/2012 | Yanev et al. | |
| 2012/0226472 A1 | 9/2012 | Yuen et al. | |
| 2014/0052475 A1 | 2/2014 | Madan et al. | |
| 2014/0247989 A1 | 9/2014 | Deaver | |
| 2014/0313030 A1 | 10/2014 | Ten Kate et al. | |
| 2014/0377727 A1 | 12/2014 | Yom-Tov et al. | |
| 2015/0037315 A1 | 2/2015 | Matharu et al. | |
| 2015/0313529 A1 | 11/2015 | Nevo et al. | |
| 2015/0314102 A1 | 11/2015 | Rosenberg et al. | |
| 2015/0370993 A1 | 12/2015 | Moturu et al. | |
| 2016/0001096 A1 | 1/2016 | Mishelevich et al. | |
| 2016/0063205 A1 | 3/2016 | Moturu et al. | |
| 2016/0063874 A1 | 3/2016 | Czerwinski | |
| 2016/0120732 A1 | 5/2016 | Hathorn | |
| 2016/0140320 A1 | 5/2016 | Moturu et al. | |
| 2016/0317781 A1 | 11/2016 | Proud | |
| 2017/0035346 A1 | 2/2017 | Apte et al. | |
| 2017/0109437 A1 | 4/2017 | Kudo et al. | |
| 2017/0281060 A1 | 10/2017 | Wedekind et al. | |
| 2017/0329933 A1 | 11/2017 | Brust et al. | |
| 2017/0340270 A1 | 11/2017 | Ganesh | |
| 2018/0052962 A1 | 2/2018 | Van der Koijk et al. | |
| 2018/0060494 A1 | 3/2018 | Dias et al. | |
| 2018/0089385 A1 | 3/2018 | Gupta et al. | |
| 2018/0107793 A1* | 4/2018 | Ni | G16H 20/00 |
| 2018/0107936 A1 | 4/2018 | Chattopadhyay | |
| 2018/0122510 A1 | 5/2018 | Apte et al. | |
| 2018/0211012 A1 | 7/2018 | Malhotra et al. | |
| 2018/0285528 A1 | 10/2018 | Healey et al. | |
| 2018/0330824 A1 | 11/2018 | Athey et al. | |
| 2018/0357562 A1 | 12/2018 | Hofman | |
| 2018/0358119 A1* | 12/2018 | Bhushan | G16H 40/63 |
| 2019/0019581 A1 | 1/2019 | Vaughan et al. | |
| 2019/0021641 A1 | 1/2019 | Feuerstein | |
| 2019/0043610 A1 | 2/2019 | Vaughn | |
| 2019/0050774 A1 | 2/2019 | Divine et al. | |
| 2019/0066834 A1 | 2/2019 | Van Tuyl et al. | |
| 2019/0088366 A1 | 3/2019 | Vaughn et al. | |
| 2019/0109830 A1 | 4/2019 | McFarland et al. | |
| 2019/0142338 A1 | 5/2019 | Fang et al. | |
| 2019/0159716 A1 | 5/2019 | Alailima et al. | |
| 2019/0216392 A1 | 7/2019 | Bower et al. | |
| 2019/0236923 A1 | 8/2019 | Devdas et al. | |
| 2019/0262218 A1 | 8/2019 | Hathorn | |
| 2019/0298917 A1 | 10/2019 | Malave et al. | |
| 2019/0307844 A1 | 10/2019 | Pereira | |
| 2019/0313934 A1 | 10/2019 | Lee et al. | |
| 2019/0335006 A1 | 10/2019 | George et al. | |
| 2019/0341152 A1 | 11/2019 | Mellem et al. | |
| 2019/0388733 A1 | 12/2019 | Ackland | |
| 2020/0082735 A1 | 3/2020 | Nel et al. | |
| 2020/0082927 A1 | 3/2020 | Hernandez | |
| 2020/0219605 A1 | 7/2020 | Govindjee | |
| 2020/0245009 A1 | 7/2020 | Saini et al. | |
| 2020/0303046 A1* | 9/2020 | Martinez | G16H 10/60 |
| 2020/0411185 A1 | 12/2020 | Oser et al. | |
| 2021/0020294 A1* | 1/2021 | Bharmi | G16H 50/30 |
| 2021/0145338 A1 | 5/2021 | Borthakur | |
| 2021/0177324 A1 | 6/2021 | Levy | |
| 2021/0183481 A1 | 6/2021 | Levy | |
| 2021/0183482 A1 | 6/2021 | Levy | |
| 2021/0183512 A1 | 6/2021 | Van Dusen | |
| 2021/0217508 A1 | 7/2021 | Kosofsky et al. | |
| 2021/0321883 A1* | 10/2021 | Mcmahan | A61B 5/02055 |
| 2021/0375424 A1 | 12/2021 | Levy | |
| 2021/0375465 A1 | 12/2021 | Levy | |
| 2022/0028528 A1 | 1/2022 | Paull et al. | |
| 2022/0028529 A1 | 1/2022 | Paull et al. | |
| 2022/0028541 A1 | 1/2022 | Paull et al. | |
| 2022/0130510 A1 | 4/2022 | Levy | |
| 2022/0130513 A1 | 4/2022 | Levy | |
| 2022/0130514 A1 | 4/2022 | Levy | |
| 2022/0130515 A1 | 4/2022 | Levy | |
| 2022/0130516 A1 | 4/2022 | Levy | |
| 2022/0130539 A1 | 4/2022 | Levy | |

FOREIGN PATENT DOCUMENTS

| | | |
|---|---|---|
| JP | 4781710 | 7/2011 |
| JP | 2017/521756 | 8/2017 |
| JP | 6684820 | 1/2020 |
| KR | 10-2018-0006692 | 1/2018 |
| KR | 10-2019-0009946 | 1/2019 |
| WO | WO 2007/130491 | 11/2007 |
| WO | WO 2010/009278 | 1/2010 |
| WO | WO 2011/105914 | 9/2011 |
| WO | WO 2017/106770 | 6/2017 |
| WO | WO 2017/214630 | 12/2017 |
| WO | WO 2018/071886 | 4/2018 |
| WO | WO 2018/077844 | 5/2018 |
| WO | WO 2019/040918 | 2/2019 |
| WO | WO 2019/123463 | 6/2019 |
| WO | WO 2021/032327 | 2/2021 |

OTHER PUBLICATIONS

Brown, A. M., "An App for Every Psychological Problem: Vision for the Future" (Order No. 10032397). Available from ProQuest Dissertations and Theses Professional. (1773418320). Retrieved from https://dialog.proquest.com/professional/docview/1773418320?accountid=131444 (Year: 2016).

Burkhouse et al., Neural Reactivity to Reward as a Predictor of Cognitive Behavioral Therapy Response in Anxiety and Depression, Depress Anxiety, 33(4), 281-288, Apr. 2016 (Year: 2016).

Everitt et al., "Assessing Cognitive behavioural Therapy in Irritable Bowel (ACTIB): protocol for . . . irritable bowel syndrome in

(56) References Cited

OTHER PUBLICATIONS adults", May 2015, PubMed Central, BMJ Open. 2015; 5(7): e008622. (Year: 2015).

* cited by examiner

METHOD AND SYSTEM FOR REMOTELY IDENTIFYING AND MONITORING ANOMALIES IN THE PHYSICAL AND/OR PSYCHOLOGICAL STATE OF AN APPLICATION USER USING BASELINE PHYSICAL ACTIVITY DATA ASSOCIATED WITH THE USER

RELATED APPLICATIONS

This application is related to U.S. patent application Ser. No. 16/888,099, naming Simon Levy as inventor, filed concurrently with the present application on May 29, 2020, entitled "METHOD AND SYSTEM FOR REMOTELY IDENTIFYING AND MONITORING ANOMALIES IN THE PHYSICAL AND/OR PSYCHOLOGICAL STATE OF AN APPLICATION USER USING AVERAGE PHYSICAL ACTIVITY DATA ASSOCIATED WITH A SET OF PEOPLE OTHER THAN THE USER," which is hereby incorporated by reference in its entirety as if it were fully set forth herein. This application is also related to U.S. patent application Ser. No. 16/888/104, naming Simon Levy as inventor, filed concurrently with the present application on May 29, 2020, entitled "METHOD AND SYSTEM FOR REMOTELY MONITORING THE PHYSICAL AND PSYCHOLOGICAL STATE OF AN APPLICATION USER USING ALTITUDE AND/OR MOTION DATA AND ONE OR MORE MACHINE LEARNING MODELS," which is hereby incorporated by reference in its entirety as if it were fully set forth herein.

BACKGROUND

In recent years, digital applications have come to play an increasingly large role in the daily lives of billions of people all over the world. Currently, a vast number of applications are readily available over a wide variety of technologies. These applications range greatly in type and purpose, providing users of these applications with information and services, such as productivity tools, educational materials, and entertainment options. As technology advances, these applications are becoming more and more sophisticated in terms of the content and experiences they are able to deliver. For example, in addition to providing users with information and other types of static content, many modern applications also provide a variety of interactive features which allow a user to receive and interact with specific and/or customized content based on user input and user behavior. As such, the benefits an application is able to provide to a user can be customized to meet the needs or desires of specific individuals.

Due to the increased use of these digital applications in the daily lives of their users, many such applications are now being used to supplement or replace traditional human to human and in person interactions. Further, it has become increasingly clear that this trend will continue to grow in the years to come. However, while these types of interactive applications provide many beneficial features to users, currently, these applications still present a variety of limitations that need to be addressed in order for this interactive technology to achieve its fullest potential.

As a specific example, every day, millions of people are diagnosed with a wide variety of medical conditions, ranging greatly in type and severity. A patient who has been diagnosed with a medical condition often experiences many hardships as a result of their diagnosis. In addition to physical effects, such as pain, discomfort, or loss of mobility, which may accompany the diagnosis, the hardships faced by patients often further include financial difficulties resulting from lost work, medical bills and the cost of treatments. Further still, a patient's diagnosis often negatively impacts their social interactions and overall emotional well-being. The result is that many patients experience significant psychological distress as a result of their diagnosis, and they often do not receive adequate support or treatment to alleviate this distress.

Often, when a patient is diagnosed with one or more medical conditions by a medical care provider or medical specialist, the patient may also be referred to additional health professionals for further care and treatment. For example, a patient may be referred to a psychologist, psychiatrist, counselor, or other mental health professional. A patient may also be directed to one or more support groups to assist with any psychological distress that the patient may be experiencing. While these traditional face-to-face options may be greatly beneficial to a patient, often times they do not provide enough support. For example, when a patient is alone, at home, or not otherwise engaged directly with a health professional or support group, they may experience a significant degree of one or more negative emotional states, such as fear, anxiety, panic, and depression. Further, these negative emotional states may be specifically related to symptoms associated with their medical condition or changes in symptoms associated with their medical condition. Left unidentified and untreated, these negative emotional states often exacerbate the patient's physical symptoms, which in turn can lead to greater psychological distress.

Additionally, many patients who have been diagnosed with a physical or psychological condition are prescribed one or more medications to help alleviate any pain, discomfort, or distress that the patient may be experiencing. While medications can provide many benefits to patients, many medications also produce a variety of physical and psychological side effects, which often hinder the patient's treatment and recovery.

Consequently, tracking and monitoring of a patient's various physical and mental states is often a vital part of ensuring proper diagnosis and treatment. Some patients may readily recognize changes in symptoms associated with their medical conditions by actively tracking and monitoring their own physical and mental states, which may lead them to seek out supplementary help. However, many patients either lack the tools or are otherwise unable to actively track and monitor their own physical and mental states. As a result, many patients experience changes in their symptoms without recognizing them, and thus might not realize that they are in need of supplementary help. Further, many patients may feel embarrassed or ashamed about their medical conditions, which may discourage them from actively reaching out for the help that they need.

Because current mechanisms for enabling health professionals to remotely monitor the physical and psychological states of patients outside of a medical office or support group setting are limited, the shortcomings associated with these traditional support and treatment options can have significant and serious effects on a patient's overall health, safety, and well-being. As a result, the lack of adequate mechanisms for remotely monitoring and tracking the physical and psychological states of patients presents a technical problem, which requires a technical solution. As digital applications begin to replace human interactions, this problem becomes even more pronounced. This is because people are increasingly relying on applications to provide them with support and assistance in a wide variety of aspects of their daily lives, and the failure of traditional solutions to address these issues has the potential to lead to significant consequences for a large number of people.

In addition, as evidenced by recent global events such as the current COVID-19 pandemic, there are times when large numbers of people are either restricted from meeting with their health professionals in person, are unable to travel to meet with their health professionals in person, or are unwilling to take the unnecessary risks involved in placing themselves in an environment where a virus or disease may be more easily communicable. As a result, there is an ever increasing demand for health professionals to have a wider variety of tools at their disposal for effectively interacting remotely with their patients.

What is needed is a method and system to more accurately and remotely identify and monitor changes or anomalies in a patient's physical and psychological states in order to ensure that patients receive adequate care, support, and treatment.

SUMMARY

Embodiments of the present disclosure utilize digital therapeutics to provide an effective and efficient technical solution to the technical problem of accurately and remotely identifying and monitoring changes or anomalies in the physical and/or psychological state of a current user of one or more applications, such as a patient. Digital therapeutics can be generally defined as a treatment or therapy that utilizes digital and/or Internet-based health technologies to drive meaningful patient health outcomes or improvements.

In the embodiments disclosed herein, one or more digital therapeutics applications are utilized to monitor altitude and/or motion data received from a device associated with the current user to obtain current device altitude and/or motion data. In one embodiment, the current device altitude and/or motion data is then utilized to identify one or more physical activities in which the user is engaging. Further, the current device altitude and/or motion data may be analyzed to generate current physical activity data, such as physical activity count data, physical activity speed, velocity, and/or acceleration data, and/or physical activity length data. In one embodiment, the current user's physical activity data is compared with the current user's own historical baseline physical activity data to determine the current user's physical and/or mental state and to detect any anomalies in the current user's physical and/or mental state. In another embodiment, the current user's physical activity data is compared with average physical activity data associated with a set of people other than the user to determine the current user's physical and/or mental state and to detect any anomalies in the current user's physical and/or mental state. In yet another embodiment, the current user's altitude data, motion data, and/or physical activity data is processed using one or more machine learning based prediction models to determine the current user's physical and/or mental state and to detect any anomalies in the current user's physical and/or mental state.

Embodiments of the present disclosure provide an effective and efficient technical solution to the technical problem of accurately and remotely identifying and monitoring changes or anomalies in the physical and/or psychological state of patients who have been diagnosed with one or more medical conditions. In the disclosed embodiments, a patient diagnosed with one or more medical conditions is prescribed access to a digital therapeutics application, which is designed to provide guided care to the patient in a variety of ways, as will be discussed herein. In one embodiment, once a patient has been prescribed access to the digital therapeutics application, the patient is free to access the application and utilize the tools provided by the application. Once the patient accesses the application, the patient becomes a user of the application, and may be provided with digital content through a user interface of the application. The content provided to the user may include information relating to one or more of the user's medical conditions, as well as information relating to the user's current and potential medications and/or treatments. The content provided to the user may further include interactive content, such as questions or exercises related to the content, which are designed to encourage the user to interact with a variety of multi-media materials through the application interface.

In one embodiment, altitude and/or motion data is received from one or more devices associated with the user, and the device altitude and motion data is utilized to determine one or more physical activities being performed by the user. Physical activities may include activities such as, but not limited to, standing, walking, running, exercising, pacing, sitting, eating, urinating, defecating, bathing, lying down, and sleeping. Data associated with these physical activities may also be determined, such as, but not limited to, physical activity count data representing the number of times a physical activity is performed by the user in a defined timeframe, physical activity speed data representing the speed, velocity, and/or acceleration at which a physical activity is performed by the user, and/or physical activity length data representing the length of time that the user spends engaging in a physical activity.

In some embodiments, once a user has been prescribed access to the digital therapeutics application, a user profile is generated for that particular user. As the user performs physical activities, altitude and/or motion data associated with one or more of the user's devices is received and analyzed to generate physical activity data, such as physical activity count data, physical activity speed, velocity, and/or acceleration data, and physical activity length data. The altitude data, motion data, and/or physical activity data may then be stored in a database associated with the user's profile. The altitude data, motion data, and/or physical activity data is then analyzed to determine baseline physical activity data for the user. The user's baseline physical activity data may be periodically or continually updated over time. Upon allowing their current physical activities to be monitored, each time the user performs a particular physical activity, current physical activity data is generated and may be compared to the user's baseline physical activity data to determine whether the user's current physical activity data is within a predefined threshold of the user's baseline physical activity data. Upon a determination that the user's current physical activity data differs from the user's baseline physical activity data outside of the predefined threshold, a prediction may be made, based on this determination, as to the likely physical and/or mental state of the user, and additional actions may be taken, as will be discussed in further detail below.

In some embodiments, average physical activity data may be generated or obtained representing an average number of occurrences, an average speed, velocity, and/or acceleration, and/or an average length of engagement associated with one or more physical activities in a defined timeframe for a particular set of people. A particular set of people may include, as one example, a set of people with one or more medical conditions that are the same as or substantially similar to a medical condition of the user. Once the user has been prescribed access to the digital therapeutics application, they may choose to allow their current physical activities to be monitored. As the user performs physical activities, altitude and/or motion data associated with one or more of the user's devices is received and analyzed to generate current physical activity data, such as physical activity count data, physical activity speed, velocity, and/or acceleration data, and physical activity length data. Each time the user performs a particular physical activity, the user's current physical activity data may be compared to the average physical activity data associated with the particular physical activity and particular set of people. Upon a determination that the user's current physical activity data differs from the average physical activity data outside of a predefined threshold, a prediction may be made, based on this determination, as to the likely physical and/or mental state of the application user, and additional actions may be taken, as will be discussed in further detail below.

In some embodiments, device altitude and/or motion data is received from one or more devices associated with one or more application users, and for each of those users, corresponding mental and physical state data is collected, for example, through a user interface of the digital therapeutics application. The mental and physical state data is then correlated with the device altitude and/or motion data, and the correlated user data is utilized as training data to generate one or more trained machine learning based mental and/or physical state prediction models. In one embodiment, the device altitude and/or motion data is first processed to generate physical activity data, such as physical activity count data, physical activity speed, velocity, and/or acceleration data, and physical activity length data. The mental and physical state data is then correlated with the physical activity data and the correlated user data is utilized as training data to generate one or more trained machine learning based mental and/or physical state prediction models.

Once one or more trained machine learning based mental and/or physical state models have been generated, a current user of the digital therapeutics application may choose to allow their current physical activities to be monitored. As the user performs physical activities, altitude and/or motion data associated with one or more of the user's devices is received and may further be analyzed to generate current physical activity data associated with the current physical activities of the user. The current user's device altitude data, device motion data, and/or physical activity data is then provided to the one or more trained machine learning based mental and/or physical state prediction models, resulting in the generation of mental state prediction data and/or physical state prediction data for the current user. Based, at least in part, on the mental and/or physical state prediction data, additional actions may be taken, as will be discussed in further detail below.

In various embodiments, upon either identifying the likely physical or mental state of a user, or identifying a change or anomaly in the physical or mental state of a user, additional actions may be taken by the digital therapeutics application to assist the user, depending on factors such as, but not limited to, the user's particular physical state, mental state, known medications, and/or known medical conditions. Actions to be taken may further depend upon a determination of the severity of the change or anomaly. As one illustrative example, if a user has been diagnosed with a medical condition that affects the user's digestive system, the physical activity data associated with the user may indicate that the user is using the bathroom with increasing frequency and urgency, and actions may be taken to deliver tailored content to the user regarding the progression of the user's disease or diagnosis based on the current physical state of the user.

As another illustrative example, the user's physical activity data may indicate that the user is frequently pacing back and forth, and a determination may be made that the user is anxious or fearful. If a determination is made that a user is in a mildly anxious mental state, minor actions may be taken, such as adjusting the content and/or presentation of information that is being provided to the user through a user interface of the application. On the other hand, if a determination is made that the user is currently in a severely anxious, fearful, or depressed state, more extreme actions may be taken, such as notifying one or more medical professionals associated with the user through a notification system of the application, or some other form of personal intervention from one or more medical professionals associated with the user. The user may also be provided with predictions related to potential future physical and/or mental states of the user, based on the current and historical physical activity data. Additionally, the physical activity data can be used to determine the appropriate timing of the notifications and content being provided to the user.

In addition to the above, in some embodiments, the user's physical activity data may also be utilized to verify the identity of the user. For example, if the user's current physical activity data is well outside of a predefined threshold of the user's baseline physical activity data, it may be determined that someone other than the user is using the application without authorization, and appropriate actions would be taken.

As a result of these and other disclosed features, which are discussed in more detail below, the disclosed embodiments provide an effective and efficient technical solution to the technical problem of remotely identifying and monitoring changes or anomalies in the physical and psychological state of application users, including users who have been diagnosed with one or more medical conditions.

Figure 1A:
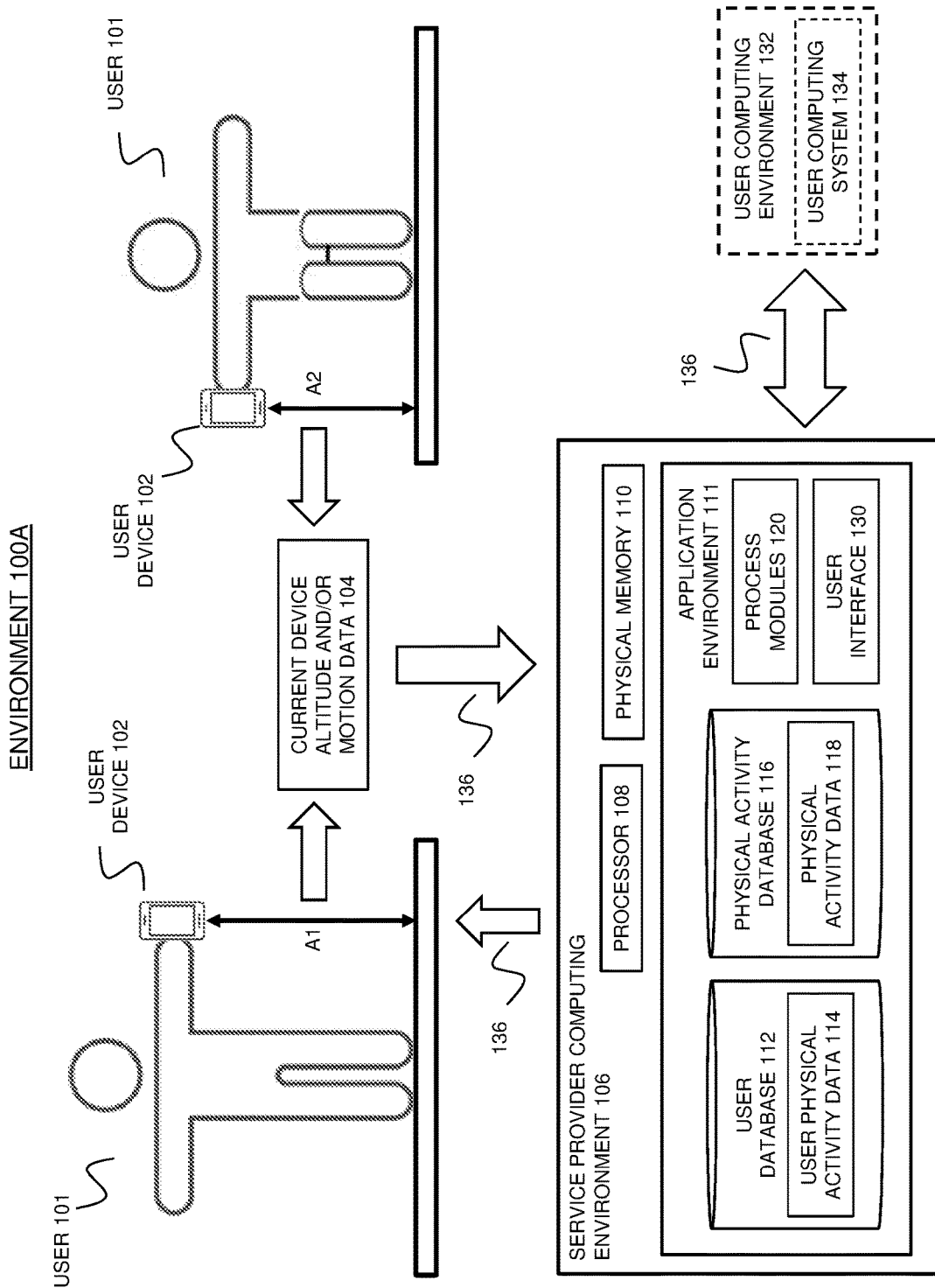
FIG. 1A is a high-level block diagram of an environment for remotely identifying and monitoring anomalies in the physical and/or psychological state of an application user, in accordance with one embodiment.

Common reference numerals are used throughout the figures and the detailed description to indicate like elements. One skilled in the art will readily recognize that the above figures are merely illustrative examples and that other architectures, modes of operation, orders of operation, and elements/functions can be provided and implemented without departing from the characteristics and features of the invention, as set forth in the claims.

DETAILED DESCRIPTION

Embodiments will now be discussed with reference to the accompanying figures, which depict one or more exemplary embodiments. Embodiments may be implemented in many different forms and should not be construed as limited to the embodiments set forth herein, shown in the figures, or described below. Rather, these exemplary embodiments are provided to allow a complete disclosure that conveys the principles of the invention, as set forth in the claims, to those of skill in the art.

Embodiments of the present disclosure provide an effective and efficient technical solution to the technical problem of remotely identifying and monitoring changes or anomalies in the physical and/or psychological state of one or more application users. In the disclosed embodiments, a user is granted access to one or more applications designed to provide the user with information and assistance in a variety of ways. Altitude and/or motion data is collected from one or more devices associated with the user, and the device altitude and/or motion data is analyzed to identify physical activities being performed by the user. In some embodiments, physical activity data related to the identified physical activities is generated based on the device altitude and/or motion data, such as, but not limited to, physical activity count data, physical activity speed, velocity, and/or acceleration data, and physical activity length data. The physical activity data is then analyzed to identify and monitor changes or anomalies in the physical and/or psychological state of the user using baseline physical activity data and/or average physical activity data. In some embodiments, machine learning models are utilized to identify and/or predict the physical and/or psychological state of the user. Upon identification of changes or anomalies in the user's physical and/or psychological state, one or more actions are taken to provide the user with information and alerts, or to otherwise assist the user.

System Overview

FIG. 1A is a high-level block diagram of an environment 100A for remotely identifying and monitoring anomalies in the physical and/or psychological state of an application user, in accordance with one embodiment.

In one embodiment, environment 100A includes user 101, user device 102, service provider computing environment 106 and, optionally, user computing environment 132 and user computing system 134. Service provider computing environment 106 includes application environment 111, processor 108, and physical memory 110. Processor 108 and physical memory 110 coordinate the operation and interaction of the various data and data processing modules associated with application environment 111. In one embodiment, application environment 111 includes user database 112, physical activity database 116, user interface 130, and one or more process modules 120. In one embodiment, user database 112 includes user physical activity data 114 and physical activity database 116 includes physical activity data 118.

In various embodiments, current device altitude and/or motion data 104 is obtained from user device 102 associated with user 101 and provided to application environment 111 over one or more communications networks 136. The one or more communications networks 136 may include networks and systems such as, but not limited to, cellular communications networks, satellite communications networks, Wi-Fi communications networks, Bluetooth communications networks, GPS communications networks and/or any other type of communications networks or systems that may be developed after the time of filing. Upon receipt of the current device altitude and/or motion data 104 by application environment 111, the current device altitude and/or motion data 104 may be stored in user database 112. The current device altitude and/or motion data 104 may be further processed and analyzed to generate at least part of user physical activity data 114. In one embodiment, portions of the user physical activity data 114 are compared with physical activity data 118 stored in physical activity database 116. The various data processing, data analysis, and data comparison operations, which will be described in further detail below, may be coordinated by one or more of the process modules 120.

In one embodiment, user interface 130 of application environment 111 may be configured to provide and receive information from user device 102, but may also be configured to provide and receive information from a user computing system 134 of user computing environment 132, which may be separate from the user device 102 that is used to collect current device altitude and/or motion data 104.

The components and features of FIG. 1A are discussed in more detail below with respect to various embodiments.

I. Methods and Systems Using the User's Own Baseline Physical Activity Data

Figure 1B:
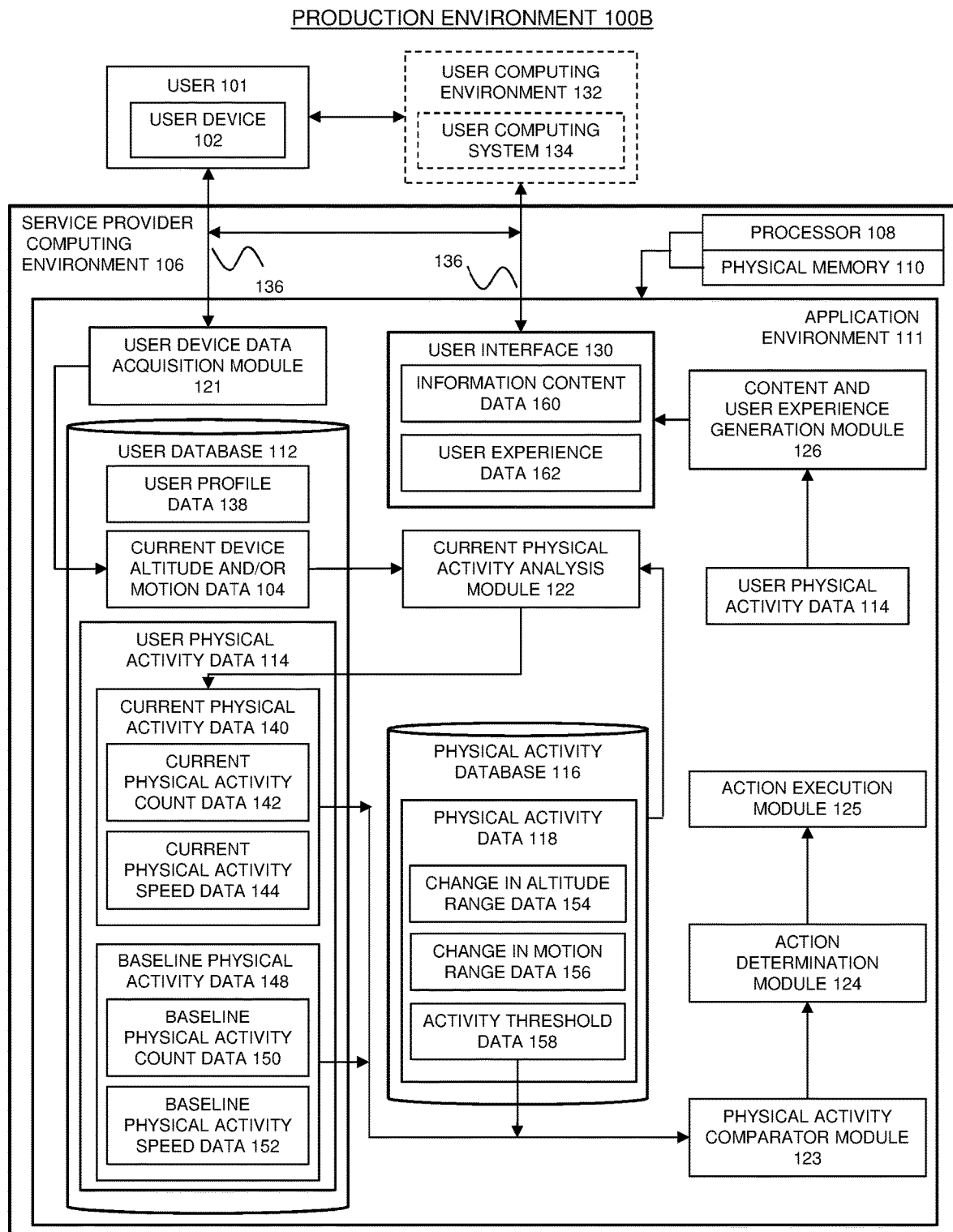
FIG. 1B is a block diagram of a production environment for remotely identifying and monitoring anomalies in the physical and/or psychological state of an application user using baseline physical activity data associated with the user, in accordance with one embodiment.
Figure 2:
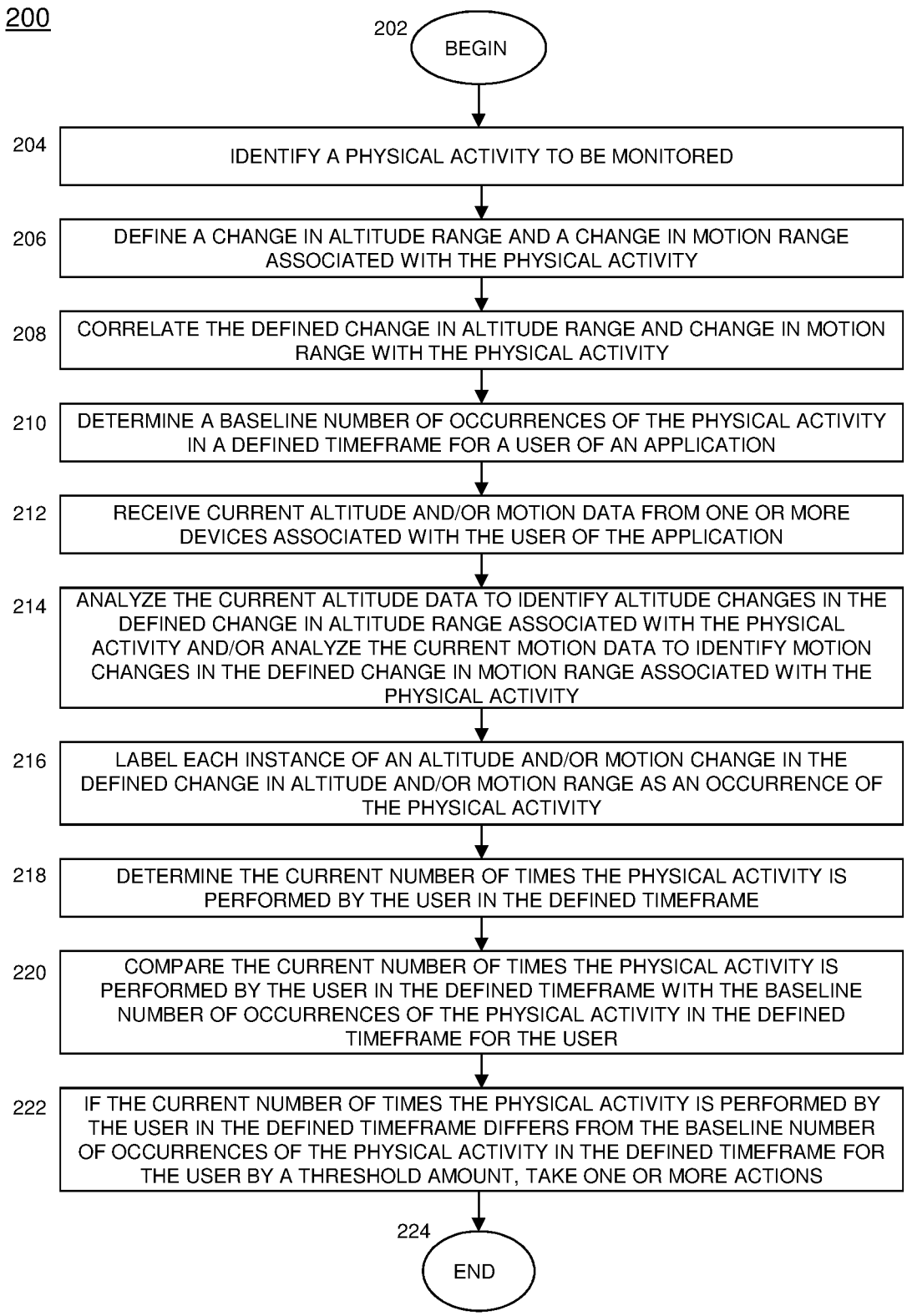
FIG. 2 is a flow chart of a process for remotely identifying and monitoring anomalies in the physical and/or psychological state of an application user using baseline physical activity data associated with the user, in accordance with one embodiment.

In some embodiments, the physical and/or psychological state of a user is remotely identified and monitored by comparing the user's current physical activity data with the user's own historic baseline physical activity data. FIGS. 1A, 1B, and 2 depict one illustrative example of a method and system for remotely identifying and monitoring anomalies in the physical and/or psychological state of an application user using baseline physical activity data associated with the user.

FIG. 1B is a block diagram of a production environment 100B for remotely identifying and monitoring anomalies in the physical and/or psychological state of an application user using baseline physical activity data associated with the user, in accordance with one embodiment.

Referring to FIGS. 1A and 1B together, in one embodiment, production environment 100B includes user 101, user device 102, service provider computing environment 106 and, optionally, user computing environment 132 and user computing system 134. Service provider computing environment 106 includes application environment 111, processor 108, and physical memory 110. Processor 108 and physical memory 110 coordinate the operation and interaction of the data and data processing modules associated with application environment 111.

In one embodiment, application environment 111 includes user database 112. User database 112 further includes user profile data 138, current device altitude and/or motion data 104, and user physical activity data 114. User physical activity data 114 further includes current physical activity data 140 and baseline physical activity data 148. In the illustrative embodiment of FIG. 1B, current physical activity data 140 includes current physical activity count data 142 and current physical activity speed data 144, and baseline physical activity data 148 includes baseline physical activity count data 150 and baseline physical activity speed data 152, each of which will be discussed in further detail below. As used herein, the terms speed data or motion data can include, but are not limited to, data representing the speed, velocity, and/or acceleration associated with a user, such as user 101, and received from a user device, such as user device 102. Although not depicted in the illustrative embodiment of FIG. 1B, current physical activity data 140 and baseline physical activity data 148 may include additional data, such as, but not limited to, current physical activity length data and baseline physical activity length data.

In one embodiment, application environment 111 further includes physical activity database 116. Physical activity database 116 includes physical activity data 118, which further includes data such as, but not limited to, change in altitude range data 154, change in motion range data 156, and activity threshold data 158. In one embodiment application environment 111 also includes user interface 130, which may be utilized to provide information content data 160 and/or user experience data 162 to user device 102 associated with user 101 and/or to user computing system 134 associated with user 101, over one or more communications networks 136.

In one embodiment, application environment 111 further includes one or more process modules 120. Process modules 120 may include, but are not limited to, user device data acquisition module 121, current physical activity analysis module 122, physical activity comparator module 123, action determination module 124, action execution module 125, and content and user experience generation module 126, each of which will be discussed in further detail below.

FIG. 2 is a flow chart of a process 200 for remotely identifying and monitoring anomalies in the physical and/or psychological state of an application user using baseline physical activity data associated with the user, in accordance with one embodiment.

Referring to FIG. 2, process 200 begins at BEGIN 202 and process flow proceeds to 204. In one embodiment, at 204, one or more physical activities are identified, which are activities to be monitored for a user of an application. Examples of physical activities to be monitored include activities such as, but not limited to, standing, walking, running, exercising, pacing, sitting, eating, urinating, defecating, bathing, lying down, and sleeping. In various embodiments, specific physical activities may be selected for monitoring based on a variety of factors, such as the needs of a particular user or group of users. For example, in some embodiments, the user is a patient who has been diagnosed with one or more medical conditions, and it may be determined that certain physical activities will be affected by the patient's medical condition, medications, and/or medical history. Further, certain physical activities may also be affected by a patient's psychological state. Consequently, monitoring of a patient's physical activities can often yield valuable information that can assist in a patient's treatment and care.

As illustrative examples, a patient who is experiencing symptoms related to digestive system functions may have an increase or decrease in frequency or urgency of bowel movements, and a patient who is on a medication that is a known diuretic may have an increase in the frequency or urgency of the need to urinate. Further, a patient who is experiencing high levels of anxiety may exhibit increased pacing activity, and a patient who is experiencing depression may spend a disproportionate amount of time lying in bed or sleeping. Thus, in one embodiment, at 204, the one or more physical activities that are selected for monitoring may be specific to one or more known health conditions of a user. Further, in one embodiment, at 204, the health conditions of a user may be unknown, and so a wide range of physical activities may be selected for monitoring in order to assist with diagnosis. It should be noted here, that the foregoing examples are given for illustrative purposes only, and are not intended to limit the scope of the invention as disclosed herein and as claimed below.

In one embodiment, once a physical activity to be monitored is identified at 204, process flow proceeds to 206. In one embodiment, at 206, a change in altitude range and a change in motion range associated with the identified physical activity are defined.

As used herein, a change in altitude range refers to a range of values that represent differences between one or more pairs of measured altitudes. Thus, in order to define a change in altitude range, differences between one or more pairs of measured altitudes over a defined period of time must be calculated. In order to calculate differences between one or more pairs of measured altitudes, the pairs of altitudes themselves must first be measured. Further, in order to measure a pair of altitudes, one or more physical points of reference must first be defined.

Referring to FIG. 1A, as one illustrative example, a device associated with a user of an application, such as user device 102 associated with user 101, may be held, worn, or otherwise affixed to user 101, and the user device 102 may be capable of taking an altitude measurement, where the altitude measurement represents the distance between a predetermined portion of the device, for example, the center of the device, and a fixed level, for example, sea level, or alternatively, the floor of a building or other structure. Once the physical points of reference are defined, a first altitude measurement A1 may be taken at a first point in time, a second altitude measurement A2 may be taken at a second point in time, and the first altitude measurement A1 and second altitude measurement A2 may be referred to as a pair of measured altitudes. The difference between the first altitude measurement A1 and second altitude measurement A2 of the pair of measured altitudes may then be calculated and is herein referred to as a change in altitude. Further, data associated with the change in altitude may also encompass the speed, velocity, and/or acceleration of the change in altitude from one value to another value.

In order to associate a change in altitude with a physical activity, multiple measurements may need to be taken while a particular person, or a variety of people, perform the physical activity, to account for variables such as a person's height and the type of device that is taking the measurements. For example, changes in altitude associated with a physical activity such as sitting or standing will vary greatly depending on a person's height and the type of device being used. A device that may be worn around a person's ankle, for example, would likely not provide useful data since the altitude of the ankle is not likely to change much depending on whether a person is standing or sitting. On the other hand, the altitude of a device that is worn on the head or other upper body part is likely to change significantly depending on whether a person is sitting or standing. Further, the altitude of a device that is held in the hand may vary depending on the position of the arm in addition to whether the person is sitting or standing, and so additional variables may need to be taken into account for handheld devices or other devices worn on the arm. Thus, the collection of altitude measurements taken while a particular person or a variety of people perform a physical activity, is referred to herein as a change in altitude range associated with the physical activity.

Referring to FIG. 1B, in some embodiments change in altitude range data 154 has been previously defined, and is simply obtained from a database, such as physical activity database 116. In other embodiments, the change in altitude range data 154 may be measured by the method and system disclosed herein, such that it can be tailored specifically to a particular user of the application, such as user 101.

Likewise, as used herein, a change in motion range refers to a range of values that represent changes in location and/or changes in speed, velocity, and/or acceleration. As noted above, as used herein, the terms speed data or motion data can include, but are not limited to, data representing the speed, velocity, and/or acceleration associated with a user, such as user 101 and received from a user device, such as user device 102. Thus, in order to define a change in motion range, changes in location and/or changes in speed, velocity, and/or acceleration over a defined period of time must be measured. As one illustrative example, a device may be held, worn, or otherwise affixed to a person, and the device may be capable of taking a location measurement, where the location measurement represents the location of the device in Euclidean space. A first location measurement may be taken at a first point in time, a second location measurement may be taken at a second point in time, and the distance between the first location measurement and the second location measurement may then be calculated. Further, the change in motion data may also encompass the speed, velocity, and/or acceleration of the change in motion. For instance, the change in motion data may include the speed at which a person moved from one location to another location. Thus, a variety of motion-related data points may be measured and collected, and this collection of data points is herein referred to as change in motion data or simply motion data.

As with the change in altitude data, in order to associate a change in motion with a physical activity, multiple measurements may need to be taken while a particular person, or a variety of people perform the physical activity. For example, changes in motion associated with a physical activity such as pacing or exercising will vary greatly depending on a wide variety of factors such as the height, weight, and body type of a particular person, and so a large number of measurements may need to be taken while one or more people perform the physical activity in order to define a range of values, herein referred to as change in motion range data 156, which is to be associated with a particular physical activity. In some embodiments change in motion range data 156 has been previously defined, and is simply obtained from a database, such as physical activity database 116. In other embodiments, change in motion range data 156 may be measured by the method and system disclosed herein, such that it can be tailored specifically to a particular user of the application, such as user 101.

Returning now to FIG. 2, in one embodiment, once a change in altitude range and a change in motion range have been defined at 206, process flow proceeds to 208. In one embodiment, at 208, the defined change in altitude range and change in motion range are correlated with the physical activity.

Returning again to FIG. 1B, the correlated data may be stored as part of physical activity data 118 in a database, such as physical activity database 116, which may contain change in altitude range and change in motion range data for a wide variety of physical activities. In some embodiments, one or more activity threshold values are also defined to generate activity threshold data 158, which may be correlated with each of the physical activities, and stored in physical activity database 116 as part of physical activity data 118. For example, a threshold value may be defined which represents the maximum allowable variation between a current measurement associated with a physical activity and an average or baseline measurement associated with the physical activity, as will be discussed in further detail below.

Returning to FIG. 2, in one embodiment, once the change in altitude range and change in motion range have been correlated with the physical activity at 208, process flow proceeds to 210. In one embodiment, at 210, a baseline number of occurrences of the physical activity in a defined timeframe are determined for a user of an application.

In one embodiment, a user of an application is provided with a user interface, which allows the user to receive output from the application, as well as to provide input to the application. In various embodiments, the application may be any type of application that is capable of providing content/information to a user through a user interface, including, but not limited to, a desktop computing system application, a mobile computing system application, a virtual reality computing system application, an application provided by an Internet of Things (IoT) device, or any combination thereof. In various embodiments, the user interface may include any combination of a graphical user interface, an audio-based user interface, a touch-based user interface, or any other type of user interface currently known to those of skill in the art, or any other type of user interface that may be developed after the time of filing.

In one embodiment, the application provided to the user is a digital therapeutics application, which is designed to assist patients who have been diagnosed with one or more medical conditions. As a specific illustrative example, upon diagnosing a patient with one or more medical conditions, a medical care professional may prescribe the patient access to the digital therapeutics application. The digital therapeutics application may be accessed by the patient through any type of computing system that is capable of providing a user interface to a user, as discussed above. Upon accessing the digital therapeutics application, the patient then becomes a user of the application, and is provided with a user interface, which enables the patient user to interact with the digital therapeutics application.

Returning again to FIG. 1B, in one embodiment, once user 101 has been granted access to the application, user profile data 138 is obtained and/or generated and a user profile is created for user 101. In some embodiments, the user profile data 138 may contain data such as, but not limited to, user 101's name, age, date of birth, gender, race, and/or occupation. The user profile data 138 may further contain data related to user 101's individual sessions with the application, or data related to user 101's interactions with the application over time. In the example of a digital therapeutics application, in some embodiments, the user profile data 138 may contain information specific to the application's field of use, such as user 101's medical history, medical conditions, medications, and/or medical care providers.

In some embodiments, the user profile may be made accessible to user 101, and user 101 may be given permissions to view and modify one or more parts of the profile. In other embodiments, the user profile is not made accessible to user 101, and is instead maintained solely for use by the application and/or the application administrators. In other embodiments, the user profile is not made accessible to user 101, and is instead accessible only by third parties, such as one or more medical professionals. In some embodiments, some parts of the user profile may be made accessible to user 101 or third parties, while other parts of the user profile may be inaccessible by user 101 or third parties.

In one embodiment, the user profile data 138 is stored in a portion of a user database associated with user 101, such as user database 112. The user database 112 may further contain additional information related to user 101, such as historical data related to user 101's past physical activities. For example, physical activity data for user 101 may have been previously collected and stored as part of user physical activity data 114 of user database 112. User physical activity data 114 may include data such as, but not limited to, the number of times user 101 performed one or more physical activities in a given period of time, or the speed at which user 101 performed one or more physical activities for each past occurrence of each physical activity. In one embodiment, the historical physical activity data is generated through collection of altitude and motion data received from one or more devices associated with user 101 over time. In one embodiment, the historical physical activity data is provided directly by user 101, for example, through user interface 130 of the application.

In one embodiment, the historical physical activity data is analyzed to generate baseline physical activity data 148 representing one or more physical activity baselines associated with the physical activity being monitored. As noted above, physical activities being monitored may include, but are not limited to, standing, walking, running, exercising, pacing, sitting, eating, urinating, defecating, bathing, lying down, and sleeping. A variety of measurements may be utilized in the analysis of a user's physical activity data, such as, but not limited to, the number of times the user performed the physical activity in a given period of time, the speed, velocity, and/or acceleration at which the user performed the physical activity for each occurrence of the physical activity, and the length of time the user spends engaging in the physical activity for each occurrence of the physical activity.

Consider the above described illustrative example, in which the application provided to a user is a digital therapeutics application, which is designed to assist patients who have been diagnosed with one or more health conditions. In the case of a patient who has been diagnosed with a disorder that affects the patient's digestive system, the number of times per day that the patient uses the bathroom may be determined to be a useful measurement for identifying and tracking the patient's physical and/or mental state. As a further example, the speed at which the patient uses the bathroom may also be determined to be a useful measurement for identifying and tracking the patient's physical and/or mental state. Further still, if the same patient is also experiencing chronic fatigue or depression, the number of times per day that the patient sits or lies down, or the length of time the patient spends sleeping, may be determined to be useful measurements for identifying and tracking the patient's physical and/or mental state.

In the specific illustrative example describe above, several physical activities would likely be monitored for this particular patient, namely, sitting, sleeping, and defecating. Thus, the historical physical activity data associated with this particular patient would include historical data such as historical physical activity count data representing the number of times per day the patient used the bathroom to defecate, historical physical activity speed data representing the speed at which the patient used the bathroom for each occurrence of the bathroom use, historical physical activity count data representing the number of times per day the patient changed from a standing position to a sitting position, and historical physical activity length data representing the length of time the patient spent sleeping for each occurrence of the sleeping activity. Thus, the patient user may have multiple associated data points that form part of the historical physical activity data. For example, the patient user may use the bathroom 3 times on one day, and 7 times on different day, or may sleep for 7 hours on one day and 10 hours on a different day. Further, it may be considered desirable for the digital therapeutics application to group the historical physical activity data based, for example, on time segments. As such, the historical physical activity data may be analyzed for various time periods, such as the past hour, the past day, the past week, the past month, the past year, etc. Thus, the digital therapeutics application may be configured to consider a variety of factors when analyzing the historical physical activity data to generate baseline physical activity data.

As one simplified illustrative example, the digital therapeutics application may be configured to analyze user 101's historical physical activity data to calculate user 101's baseline physical activity count of the sitting activity over the past week. The application may further be configured to calculate the user's baseline physical activity count of the defecating activity over the past day. The analysis may further be configured to ignore data points that fall outside of a predefined threshold when calculating the user's baseline. The baseline physical activity counts of the sitting and defecating activities for user 101 would then be aggregated to generate baseline physical activity count data 150, which may be stored in user database 112 as part of the baseline physical activity data 148 for user 101. It should be noted again here, that the foregoing examples are given for illustrative purposes only, and are not intended to limit the scope of the invention as disclosed herein and as claimed below.

Returning now to FIG. 2, in one embodiment, once a baseline number of occurrences of the physical activity in a defined timeframe is determined for a user of the application at 210, process flow proceeds to 212. In one embodiment, at 212, current altitude and/or motion data is received from one or more devices associated with the user.

In various embodiments, a user device may be any type of device that is portable and capable of providing altitude and/or motion data, or any type of device that is portable and capable of providing raw data that can be used to calculate altitude and/or motion data, including, but not limited to, a cellular device, a handheld device, a wearable device, an implantable device, a sensor device, an accelerometer device, a motion detection device, or any other type of device currently known to those of skill in the art, or any other type of device that may be developed after the time of filing.

In one embodiment, the user device is programmed to continually collect and transmit altitude and/or motion data in real-time as the user goes about their daily activities. In one embodiment, the user device is programmed to collect and transmit altitude and/or motion data at predetermined intervals, such as once per minute, or once every 10 seconds. In some embodiments the user can determine the desired timing of data collection by entering configuration data through a user interface of the application. In some embodiments, the user may choose specific moments to collect and transmit data, or may choose when to start data collection and when to stop data collection, for example, by pushing a button on the device, toggling a switch on the device, or issuing a voice command to the device. If the device incorporates a touch screen, the user may also perform a variety of touch-based gestures to issue data collection and transmission commands to the device.

In some embodiments, the application is provided to the user on the user device, such as through a display screen of a smart phone or smart watch. In other embodiments, the user device is separate from the computing system that provides the application user interface, and the device settings may be configured through the application user interface on any type of computing system, including, but not limited to, a desktop computing system application, a mobile computing system application, a virtual reality computing system application, an application provided by an Internet of Things (IoT) device, or any combination thereof. Further, in various embodiments, the user interface may include any combination of a graphical user interface, an audio-based user interface, a touch-based user interface, or any other type of user interface currently known to those of skill in the art, or any other type of user interface that may be developed after the time of filing.

Returning to FIG. 1B, in one embodiment the current device altitude and/or motion data 104 is received from user device 102 of user 101 by user device data acquisition module 121. In various embodiments, the current device altitude and/or motion data 104 may be stored in a portion of user database 112 that is associated with user 101 for further analysis and processing.

Returning now to FIG. 2, in one embodiment, once current altitude and/or motion data is received from one or more devices associated with the user of the application at 212, process follow proceeds to 214. In one embodiment, at 214, the current altitude data is analyzed to identify altitude changes in the defined change in altitude range associated with the physical activity being monitored, and/or the current motion data is analyzed to identify motion changes in the defined change in motion range associated with the physical activity being monitored.

In various embodiments, and as used herein, the term "current altitude and/or motion data" may refer to a single altitude and/or motion measurement collected at the present moment in time. However, more typically, and in order to be useful, the current altitude and/or motion data will be comprised of several altitude and/or motion measurements occurring within a relatively short time of each other in order to facilitate the detection of changes in altitude and/or motion. For example, a first altitude measurement of the current altitude data may be compared with a second altitude measurement of the current altitude data, and the difference between the two altitude measurements may be calculated to determine whether a change in altitude is currently occurring or has recently occurred. Likewise, a first motion measurement of the current motion data may be compared with a second motion measurement of the current motion data, and the difference between the two measurements may be calculated to determine whether a change in motion is currently occurring or has recently occurred.

Upon a determination that a change in altitude and/or change in motion is currently occurring or has recently occurred, current change in altitude data may be generated representing one or more values associated with the altitude change, and/or current change in motion data may be generated representing one or more values associated with the motion change. The current change in altitude data may then be compared with the change in altitude range that was previously defined and correlated with the physical activity being monitored to determine whether the current change in altitude falls within the change in altitude range for the physical activity being monitored. Likewise, the current change in motion data may be compared with the change in motion range that was previously defined and correlated with the physical activity being monitored to determine whether the current change in motion falls within the change in motion range for the physical activity being monitored.

Returning again to FIG. 1B, in one embodiment current physical activity analysis module 122 analyzes the current device altitude and/or motion data 104 to generate current change in altitude data, which may then be compared with change in altitude range data 154 to determine whether the current change in altitude falls within the change in altitude range for the physical activity being monitored. Likewise, current physical activity analysis module 122 may analyze the current device altitude and/or motion data 104 to generate current change in motion data, which may then be compared with change in motion range data 156 to determine whether the current change in motion falls within the change in motion range for the physical activity being monitored.

Returning to FIG. 2, in one embodiment, at 214, once the current altitude data is analyzed to identify altitude changes in the defined change in altitude range associated with the physical activity being monitored, and/or the current motion data is analyzed to identify motion changes in the defined change in motion range associated with the physical activity being monitored, process flow proceeds to 216. In one embodiment, at 216, each instance of a current altitude and/or motion change that has been identified as falling with the defined change in altitude and/or motion range is labeled as an occurrence of the physical activity.

In some situations, there may be significant overlap between a change in altitude and/or motion range of one physical activity and a change in altitude and/or motion range of a different physical activity. For example, if the physical activity being monitored is related to toilet use, the change in altitude and/or motion data alone may be insufficient for determining whether the user is using the toilet or is instead, for example, sitting at a dining table. In situations like these, the addition of location data may serve to disambiguate one physical activity from another.

For example, in some embodiments, the user may provide information to the application through a user interface of the application, such as coordinates associated with specific locations related to the physical activities that are to be monitored. A user may provide several sets of coordinates associated with various rooms in the user's house, for instance. These coordinates can then be used in conjunction with the user's current altitude and/or current motion data to differentiate between various physical activities. As illustrative examples, a set of coordinates that correspond to a user's bedroom can be associated with physical activities such sleeping and lying down, a set of coordinates that correspond to a user's kitchen may be associated with physical activities such as eating, a set of coordinates corresponding to a user's bathroom may be associated with physical activities such as bathing, urinating, and defecating, etc. It should be again noted here, that the foregoing examples are given for illustrative purposes only, and are not intended to limit the scope of the invention as disclosed herein and as claimed below.

In one embodiment, once any ambiguities have been resolved and one or more occurrences of the physical activity have been identified and labeled at 216, process flow proceeds to 218. In one embodiment, at 218, the current number of times the physical activity is performed by the user in the defined timeframe is determined.

As discussed above, at operation 208 a baseline number of occurrences of the physical activity being monitored was determined for the user for a defined timeframe. Any suitable timeframe may have been selected, such that analysis of the baseline data is able to yield meaningful results. As one illustrative example, if the physical activity being monitored is sitting, the previously determined baseline data may include data indicating the average number of times per day the user changed from a standing position to a sitting position over the course of the past month. Thus, the timeframe used to calculate baseline data, i.e., per day, would be utilized at operation 218, and the current number of times the user changed from a standing position to a sitting position would be calculated for the current day.

As noted above, in addition to the number of times that a physical activity is performed, additional metrics may also be evaluated at operation 218, such as, but not limited to, the speed, velocity, and/or acceleration at which the user performed the physical activity, and the length of time that the user spent engaging in the physical activity. As another illustrative example, if the physical activity being monitored is sleeping, then it might be useful to know how many hours of sleep the user had in the current day, current week, or current month.

Returning to FIG. 1B, in one embodiment, current physical activity analysis module 122 performs the above described processing and analysis, and generates current physical activity data 140, which may be stored in the portion of user database 112 associated with user 101. Current physical activity analysis module 122 may generate current physical activity count data 142 based on the number of times that a physical activity is performed by user 101, as well as current physical activity speed data 144, based on the speed, velocity, and/or acceleration at which the user 101 performed the physical activity. In various other embodiments, additional data, such as, but not limited to, current physical activity length data may be generated, based on the length of time user 101 spent engaging in the physical activity, and this physical activity length data may also be stored as part of current physical activity data 140.

Returning now to FIG. 2, in one embodiment, once the current number of times the physical activity is performed by the user is determined for the defined timeframe at 218, process flow proceeds to 220. In one embodiment, at 220, the current number of times the physical activity was performed by the user in the defined timeframe is compared with the baseline number of occurrences of the physical activity in the defined timeframe for the user.

As noted above, baseline physical activity data that was previously determined may include a variety of data related to one or more physical activities being monitored. At 220, the baseline data for the current physical activity being monitored may be retrieved from a portion of a user database associated with the user for comparison with the current physical activity data for the current physical activity being monitored.

Returning again to FIG. 1B, for example, in one embodiment, current physical activity count data 142 may be compared to the baseline physical activity count data 150 for the physical activity being monitored, current physical activity speed data 144 may be compared to the baseline physical activity speed data 152 for the physical activity being monitored. In this example, the comparison may yield that there is no difference between the current physical activity data 140 and the baseline physical activity data 148, that there is a small difference between the current physical activity data 140 and the baseline physical activity data 148, or that there is a large difference between the current physical activity data 140 and the baseline physical activity data 148. In order to define what constitutes a "small" difference and a "large" difference, one or more activity thresholds, represented by activity threshold data 158, may first need to be defined, as will be discussed in further detail below. In the illustrative embodiment of FIG. 1B, the above described comparison is performed by physical activity comparator module 123.

Returning now to FIG. 2, in one embodiment, once the current number of times the physical activity was performed by the user in the defined timeframe is compared with the baseline number of occurrences of the physical activity in the defined timeframe for the user at 220, process flow proceeds to 222. In one embodiment, at 222, if the result of the comparison at 220 indicates that the current number of times the physical activity is performed by the user in the defined timeframe differs from the baseline number of occurrences of the physical activity in the defined timeframe for the user by a threshold amount, one or more actions are taken.

As noted above, in one embodiment, one or more activity thresholds are defined, such that when the user's current physical activity data varies from the user's baseline physical activity data, appropriate actions can be taken. In one embodiment, the one or more activity thresholds are represented by activity threshold data, which may be stored as part of a physical activity database. In one embodiment, an activity threshold represents a maximum allowable variation between a user's current physical activity data and the user's baseline physical activity data. In various embodiments, the one or more activity thresholds may be defined in various ways, such as, but not limited to, through application configuration options, or use of a predetermined standard.

For example, in one embodiment, after generation of baseline physical activity data for a user, it may be determined that the user's baseline physical activity count for the activity being monitored is 5 times per day. It may be decided by specialists, or other experts in the field of use, that a variance of 3 counts per day is relatively common, and as such, if the current physical activity data for this user indicated a physical activity count of 8 times per day or 2 times per day with respect to the physical activity being monitored, this would not raise concerns. However, if the current physical activity data for this user indicated a physical activity count of 10 times per day or 0 times per day with respect to the physical activity being monitored, this would raise concerns, and further action might be deemed appropriate, as will be discussed in further detail below. It should be noted again here, that the foregoing examples are given for illustrative purposes only, and are not intended to limit the scope of the invention as disclosed herein and as claimed below.

As already noted above, in various embodiments, multiple baselines may be generated during the generation of the baseline physical activity data, and as such, it follows from the preceding discussion that there could potentially be a different activity threshold associated with each of the individual baselines that form the baseline physical activity data.

In one embodiment, if the difference between the current physical activity data and the baseline physical activity data is greater than the activity threshold corresponding to the baseline, it may be determined that this is indicative of a change or anomaly in the physical and/or psychological state of the user, and thus one or more predictions regarding the user's current physical and/or mental state may be made. Upon identifying the current user's physical and/or mental state and/or identifying changes or anomalies in the current user's physical and/or mental state, one or more actions may be taken.

In various embodiments, if an anomaly is detected in the physical and/or psychological state of the user, several types of actions may be appropriate specifically when dealing with users who are patients diagnosed with a medical condition, and the actions to be taken may be determined based on the severity of any identified anomaly. For example, if a minor anomaly is detected in the physical and/or psychological state of the user, actions might be taken such as, but not limited to: asking the user for input and/or response data; alerting the user; providing suggestions or other information to the user; making notes in, adding data to, or highlighting the user's electronic file. On the other hand, if a major anomaly is detected in the physical and/or psychological state of the user, actions might be taken such as, but not limited to: alerting one or more of the user's mental health or medical professionals; making a specialist referral; recommending support contacts to the user; prescribing additional appointments, treatments, actions, or medications; calling emergency response or intervention professionals; notifying emergency contacts, relatives, or caregivers, etc.

In various embodiments, actions that may be taken further include delivering tailored content to the user through a user interface of the application. As already noted above, the application may be provided to the user on the same user device that is used to collect the altitude and/or motion data, however the application may instead, or in addition, be provided to the user on any type of computing system, including, but not limited to, a desktop computing system application, a mobile computing system application, a virtual reality computing system application, an application provided by an Internet of Things (IoT) device, or any combination thereof. Further, in various embodiments, the user interface may include any combination of a graphical user interface, an audio-based user interface, a touch-based user interface, or any other type of user interface currently known to those of skill in the art, or any other type of user interface that may be developed after the time of filing.

In various embodiments, the content provided to the user through the user interface includes, but is not limited to, textual information, audio information, graphical information, image information, video information, and/or any combination thereof. In one embodiment, the content is provided to the user in such a way that allows the user to interact with the provided content. For example, the user may be presented with informational content on the screen of an electronic device, along with a variety of graphical user elements, which allow the user to scroll through the informational content, click on buttons associated with the informational content, and/or enter textual strings in response to the informational content. When the informational content is presented to the user on a device that includes a touch screen, the interaction may include touch-based interactions and/or gesture recognition. In addition to textual inputs and touch or click-based inputs, in various embodiments, the user may be able to interact with the informational content through more advanced input mechanisms such as through audio input, video input, accelerometer input, voice recognition, facial recognition or through a variety of physiological sensors. Examples of physiological sensors may include, but are not limited to, heart rate monitors, blood pressure monitors, eye tracking monitors, or muscle activity monitors.

As one specific illustrative example, in one embodiment, once a user of a digital therapeutics application is provided with a user interface, they may be provided with content-based information such as, but not limited to, information related to medical history, current or potential medical care providers, medical conditions, medications, nutritional supplements, advice or suggestions regarding diet and/or exercise, or any other type of information that may be considered relevant to the user.

In one embodiment, the content-based information may be provided solely in a text format, however in various other embodiments, the user may also be presented with images that accompany the text, for example, images that depict one or more visual symptoms related to the user's medical conditions. The user may further be presented with graphical content, such charts, graphs, digital simulations, or other visualization tools. As one illustrative example, the user might be presented with a chart or graph that compares the user's symptoms with those of other patients diagnosed with the same or similar conditions. The user may further be presented with audio and/or video information related to their medical conditions. As additional illustrative examples, the user may be provided with one or more instructional videos that guide the user through physical therapy exercises, or educational videos that inform the user about the history and/or science behind their medical conditions. In various embodiments, the user may be presented with any combination of the above types of content-based information, or any other additional types of content that may be relevant to the user.

In addition to the types of content-based information discussed above, another type of data that may be presented to the user is aesthetics-based data. This type of data may not be immediately recognized by the user, but it nevertheless plays an important role in the way in which the user absorbs and reacts to the presentation of the content-based information. This aesthetics-based data is used to create the overall user experience that is provided to a user by an application, and thus may also be referred to herein as user experience data. Examples of user experience data include, but are not limited to, the colors and fonts used to present the content-based information to a user, the various shapes of the graphical user interface elements, the layout or ordering of the content-based information presented to a user, and/or the sound effects, music, or other audio elements that may accompany the presentation of or interaction with the content-based information.

As noted above, the actions to be taken may be determined based on the severity of any identified anomaly. In the case of tailoring content to the user, if the anomaly is minor, then actions might be taken to make slight adjustments to the information content data and/or the user experience data that is presented to the user. On the other hand, if the anomaly is severe, then actions might be taken to make extreme adjustments to the information content data and/or the user experience data that is presented to the user. In one embodiment, adjustments to the information content data may include adjustments such as, but not limited to, providing textual content that uses gentler language, providing audio content that includes quieter, more relaxing voices, sounds, or music, or providing image/video content that is less realistic or less graphic. Adjustments to the user experience data may include adjustments such as, but not limited to, changing the colors, fonts, shapes, presentation, and/or layout of the information content data presented to the user.

For example, in one embodiment, as discussed above, the application is a digital therapeutics application, and the user is a patient who has been diagnosed with a medical condition. Many patients experience a great deal of anxiety related to their medical conditions. If an anomaly is detected in the psychological state of the user, this may indicate that the user is experiencing a higher than normal level of anxiety, and therefore may benefit from assistance, or from adjustments designed to reduce the user's anxiety level.

As one specific illustrative example, if a determination is made that the user is slightly more anxious than they usually are, minor actions may be taken to reduce the user's anxiety level, such as adjusting the content and/or presentation of the information that is being provided to the user through the user interface. As one simplified illustrative example, cool colors such as blue and violet are known to produce calming effects, and rounder, softer shapes are also associated with calming effects. So in this situation, the user experience content data may be modified so that the content is presented to the user with a blue/violet color scheme, and the graphical user elements may be changed to include rounder and softer shapes. As another specific illustrative example, if a determination is made that the user is significantly more anxious than they usually are, more extreme actions may be taken, such as notifying one or more medical professionals associated with the user through a notification system of the application, or some other form of personal intervention from one or more medical professionals associated with the user. It should be noted again here, that the foregoing examples are given for illustrative purposes only, and are not intended to limit the scope of the invention as disclosed herein and as claimed below.

In one embodiment, in addition to determining content to provide to the user based on the identification of anomalous physical activity data, the timing of notifications, alerts, or other content delivered to the user can also be determined based on the identification of anomalous physical activity data. For example, if the physical activity data indicates that a user is using the bathroom more frequently than usual, application usage reminders, therapeutic content, and other types of notifications, alerts, or content can be delivered at specific and appropriate times. The physical activity data can also be analyzed and utilized to generate or adjust one or more content delivery schedules that are tailored specifically to the user's habits and routines.

Returning again to FIG. 1B, in one embodiment, once physical activity comparator module 123 has compared user 101's current physical activity data 140 with user 101's baseline physical activity data 148 to determine whether the difference between user 101's current physical activity data 140 and user 101's baseline physical activity data 148 is greater than the threshold in activity threshold data 158 that corresponds to the physical activity being monitored, the resulting data is analyzed and processed by action determination module 124. In one embodiment, action determination module 124 determines one or more actions that should be taken, based on the variety of factors discussed above. Upon determination of one or more actions to be taken, action execution module 125 proceeds to take any steps necessary to execute the one or more actions. Depending on the actions determined by action determination module 124, action execution module 125 may further utilize content and user experience generation module 126, which handles the generation or modification of information content data 160 and user experience data 162 based on user physical activity data 114. The information content data 160 and user experience data 162 may then be provided through user interface 130 to user device 102 associated with user 101 or to user computing system 134 associated with user 101 over the one or more communications networks 136.

Returning to FIG. 2, in one embodiment, once one or more actions are taken at 222, process flow proceeds to END 224 and the process 200 for remotely identifying and monitoring changes or anomalies in the physical and/or psychological state of an application user using baseline physical activity data is exited to await new data and/or instructions.

Figure 3:
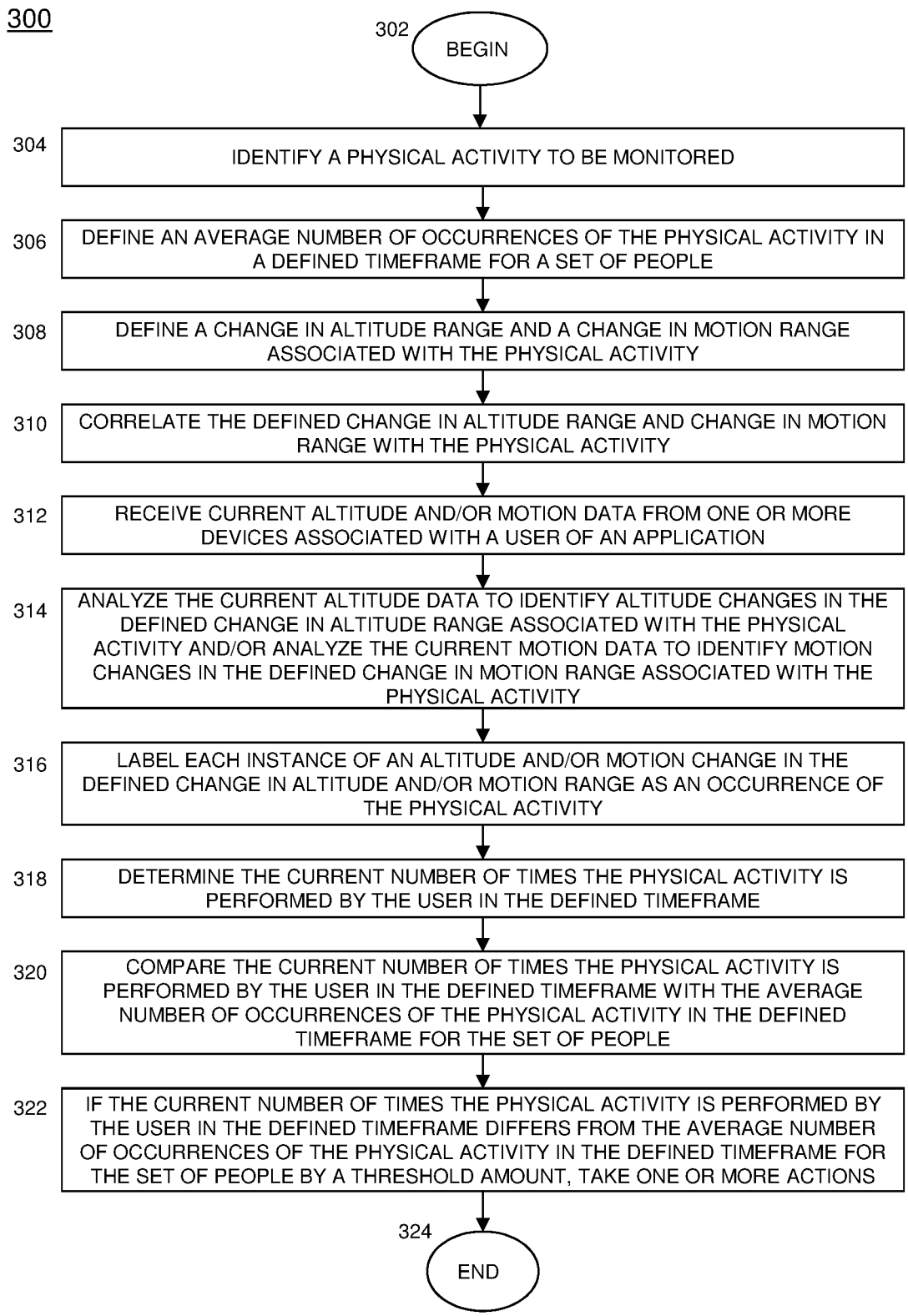
FIG. 3 is a flow chart of a process for remotely identifying and monitoring anomalies in the physical and/or psychological state of an application user using average physical activity data associated with a set of people other than the user, in accordance with one embodiment.

II. Methods and Systems Using Average Physical Activity Data of People Other than the Current User In some embodiments, the physical and/or psychological state of a user is remotely identified and monitored based on analysis and comparison of average physical activity data for a set of people other than the user's own physical activity data. Together FIGS. 1A, 1C, and 3 depict one example of a method and system for remotely identifying and monitoring anomalies in the physical and/or psychological state of an application user using average physical activity data associated with a set of people other than the user.

Figure 1C:
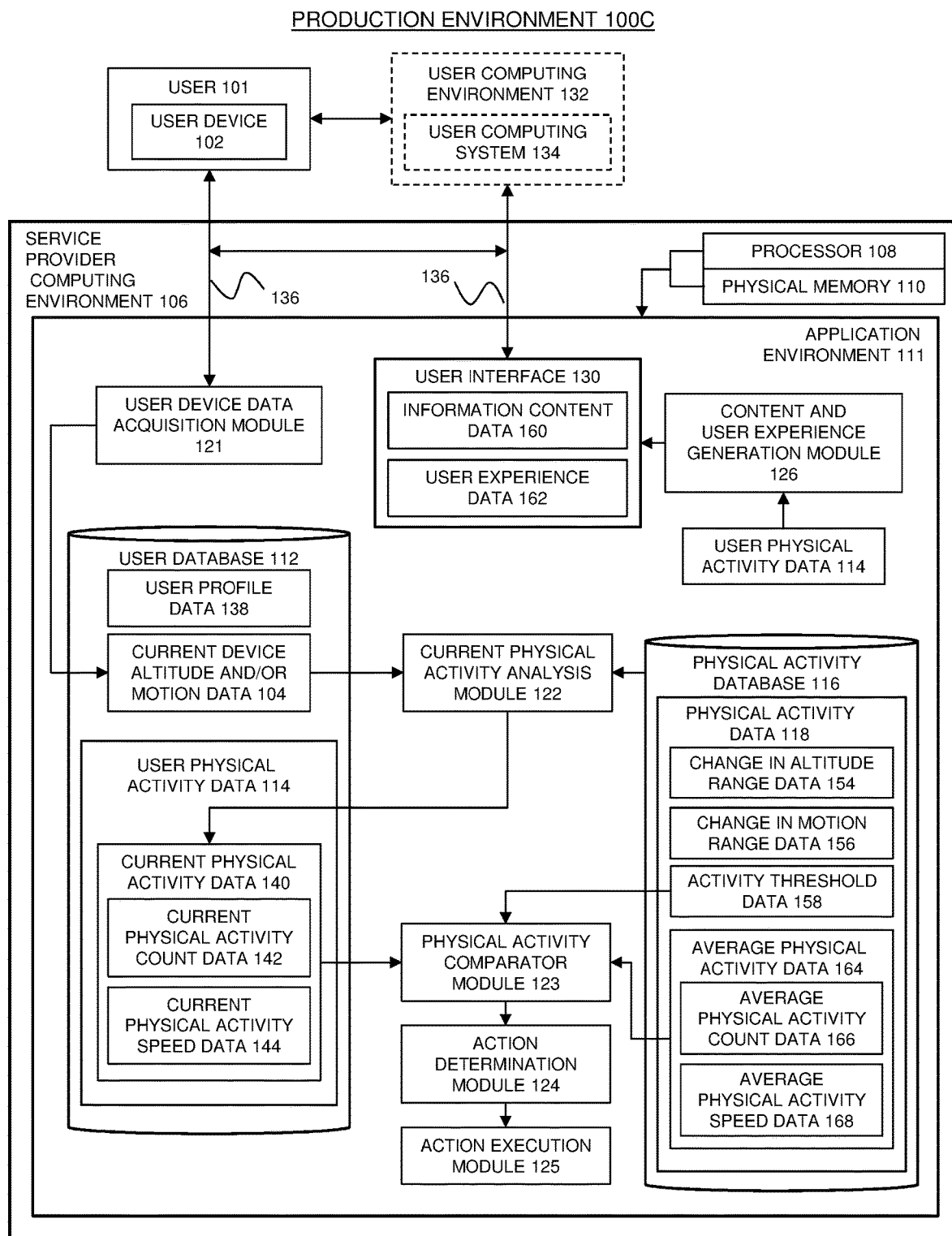
FIG. 1C is a block diagram of a production environment for remotely identifying and monitoring anomalies in the physical and/or psychological state of an application user using average physical activity data associated with a set of people other than the user in accordance with one embodiment.

FIG. 1C is a block diagram of a production environment 100C for remotely identifying and monitoring anomalies in the physical and/or psychological state of an application user using average physical activity data, in accordance with one embodiment.

Referring to FIGS. 1A and 1C together, in one embodiment, production environment 100C includes user 101, user device 102, service provider computing environment 106 and, optionally, user computing environment 132 and user computing system 134. Service provider computing environment 106 includes application environment 111, processor 108, and physical memory 110. Processor 108 and physical memory 110 coordinate the operation and interaction of the data and data processing modules associated with application environment 111.

In one embodiment, application environment 111 includes user database 112. User database 112 further includes user profile data 138, current device altitude and/or motion data 104, and user physical activity data 114. User physical activity data 114 further includes current physical activity data 140. In the illustrative embodiment of FIG. 1C, current physical activity data 140 includes current physical activity count data 142 and current physical activity speed data 144, each of which will be discussed in further detail below. Although not depicted in the illustrative embodiment of FIG. 1C, current physical activity data 140 may include additional data, such as, but not limited to, current physical activity length data.

In one embodiment, application environment 111 further includes physical activity database 116. Physical activity database 116 includes physical activity data 118, which further includes data such as, but not limited to, change in altitude range data 154, change in motion range data 156, and activity threshold data 158. In one embodiment, physical activity database 116 further includes average physical activity data 164, which itself may include average physical activity count data 166 and average physical activity speed data 168, each of which will be discussed in further detail below.

As noted above, and as used herein, the terms speed data or motion data can include, but are not limited to, data representing the speed, velocity, and/or acceleration associated with a user, such as user 101, received from a user device, such as user device 102. Although not depicted in the illustrative embodiment of FIG. 1C, average physical activity data 164 may include additional data, such as, but not limited to average physical activity length data.

In one embodiment application environment 111 also includes user interface 130, which may be utilized to provide information content data 160 and/or user experience data 162 to user device 102 associated with user 101 and/or to user computing system 134 associated with user 101, over one or more communications networks 136.

In one embodiment, application environment 111 further includes one or more process modules 120. Process modules 120 may include, but are not limited to, user device data acquisition module 121, current physical activity analysis module 122, physical activity comparator module 123, action determination module 124, action execution module 125, and content and user experience generation module 126, each of which will be discussed in further detail below.

FIG. 3 is a flow chart of a process 300 for remotely identifying and monitoring anomalies in the physical and/or psychological state of an application user using average physical activity data associated with a set of people other than the user in accordance with one embodiment. In one embodiment, process 300 begins at BEGIN 302 and process flow proceeds to 304. In one embodiment, at 304, one or more physical activities are identified, which are activities to be monitored for a user of an application. As discussed in additional detail above, examples of physical activities to be monitored include activities such as, but not limited to, standing, walking, running, exercising, pacing, sitting, eating, urinating, defecating, bathing, lying down, and sleeping. In various embodiments, specific physical activities may be selected for monitoring based on a variety of factors, such as the needs of a particular user or group of users. For example, in some embodiments, the user is a patient who has been diagnosed with one or more medical conditions, and it may be determined that certain physical activities will be affected by the patient's medical condition, medications, and/or medical history. Further, certain physical activities may also be affected by a patient's psychological state. Consequently, monitoring of a patient's physical activities can often yield valuable information that can assist in a patient's treatment and care.

In one embodiment, once a physical activity to be monitored is identified at 304, process flow proceeds to 306. In one embodiment, at 306, average physical activity count data is defined representing an average number of occurrences of the physical activity in a defined timeframe for a set of people.

Returning to FIG. 1C, in various embodiments, physical activity data may have been previously collected for a wide variety of people and stored as part of physical activity data 118 of physical activity database 116. The people whose physical activity data was previously collected may be divided into any number of sets of people. For example, if the application is a digital therapeutics application being provided to one or more patients, it may be deemed advantageous to divide people into one or more sets of people such as, but not limited to: a set of average people; a set of people with one or more of the same medical conditions; a set of people with one or more substantially similar medical conditions; a set of people with one or more of the same physical and/or mental symptoms; a set of people with one or more substantially similar physical and/or mental symptoms; a set of people taking one or more of the same medications; a set of people taking one or more substantially similar medications; a set of people that are in the same age range; a set of people that are the same sex; and a set of people that are the same ethnicity.

In one embodiment, physical activity database 116 does not include raw data for each person in a particular set of people, but instead contains calculated averages associated with each set of people. For example, physical activity data 118 may include average physical activity data 164. Average physical activity data 164 may include average physical activity count data 166, which represents the average number of times that the people in a particular set of people performed one or more physical activities in a given period of time. Average physical activity data 164 may further include average physical activity speed data 168, which represents the average speed, velocity and/or acceleration with which the people in a particular set of people performed one or more physical activities for each occurrence of the physical activity. In some embodiments, average physical activity data 164 may further include additional data such as, but not limited to, average physical activity length data representing the average length of time that the people in a particular set of people spent engaging in one or more physical activities. In one embodiment, the average physical activity data 164 may be obtained from various third parties and/or databases external to the application discussed herein. In one embodiment, the average physical activity data 164 is instead generated through collection, processing, and analysis of altitude and/or motion data received from one or more devices associated with a variety of application users over time.

Consider the above described illustrative example, in which the application provided to a user is a digital therapeutics application, which is designed to assist patients who have been diagnosed with one or more health conditions. In the case of a patient who has been diagnosed with a disorder that affects the patient's digestive system, the average number of times per day that people with the same disorder as the patient use the bathroom may be determined to be a useful measurement for comparison with the patient's current physical activity count data for physical activities related to bathroom use. As a further example, the average speed at which people taking the same medication as the patient use the bathroom may also be determined to be a useful measurement for comparison with the patient's current physical activity speed data for physical activities related to bathroom use. Further still, if the same patient is also experiencing chronic fatigue or depression, then the average number of times per day that people of the same age as the patient sit or lie down, or the average length of time that people of the same age as the patient spend sleeping, may be determined to be useful measurements for comparison with the patient's current physical activity speed data and current physical activity length data for physical activities related to sitting and sleeping. These various comparisons may then yield additional data that can assist in identifying and tracking the patient's physical and/or mental states. It should be noted again here, that the foregoing examples are given for illustrative purposes only, and are not intended to limit the scope of the invention as disclosed herein and as claimed below.

Returning now to FIG. 3, in one embodiment, once average physical activity count data is defined representing an average number of occurrences of the physical activity in a defined timeframe for a set of people at 306, process flow proceeds to 308. In one embodiment, at 308, a change in altitude range and a change in motion range associated with the identified physical activity are defined.

As discussed above, and as used herein, a change in altitude range refers to a range of values that represent differences between one or more pairs of measured altitudes. Additionally, data associated with a change in altitude may also encompass the speed, velocity, and/or acceleration of the change in altitude. In order to associate a change in altitude with a physical activity, multiple measurements may need to be taken while a particular person, or a variety of people, perform the physical activity, to account for variables such as a person's height and the type of device that is taking the measurements. Thus, the collection of altitude measurements taken while a particular person or a variety of people perform a physical activity, is referred to herein as a change in altitude range associated with the physical activity.

Returning now to FIG. 1C, in some embodiments change in altitude range data 154 has been previously defined, and is simply obtained from a database, such as physical activity database 116. In other embodiments, the change in altitude range data 154 may be measured by the method and system disclosed herein, such that it can be tailored specifically to a particular user of the application, such as user 101.

Likewise, as noted above, and as used herein, a change in motion range refers to a range of values that represent changes in location, speed, velocity, and/or acceleration associated with a user, such as user 101, and received from a user device, such as user device 102. Thus, a variety of motion-related data points may be measured and collected, and this collection of data points is herein referred to as change in motion data or simply motion data. As with the change in altitude data, in order to associate a change in motion with a physical activity, multiple measurements may need to be taken while a particular person, or a variety of people perform the physical activity, to account factors such as the height, weight, and body type of a particular person. As such, a large number of measurements may need to be taken while one or more people perform the physical activity in order to define a range of motion-related values. These motion-related values are herein referred to as change in motion range data 156, which is to be associated with a particular physical activity. In some embodiments change in motion range data 156 has been previously defined, and is simply obtained from a database, such as physical activity database 116. In other embodiments, change in motion range data 156 may be measured by the method and system disclosed herein, such that it can be tailored specifically to a particular user of the application, such as user 101.

Returning now to FIG. 3, in one embodiment, once a change in altitude range and a change in motion range have been defined at 308, process flow proceeds to 310. In one embodiment, at 310, the defined change in altitude range and change in motion range are correlated with the physical activity.

Returning again to FIG. 1C, the correlated data may be stored as part of physical activity data 118 in a database, such as physical activity database 116, which may contain change in altitude range and change in motion range data for a wide variety of physical activities. In some embodiments, one or more activity threshold values are also defined to generate activity threshold data 158, which may be correlated with each of the physical activities, and stored in physical activity database 116 as part of physical activity data 118. For example, a threshold value may be defined which represents the maximum allowable variation between a current measurement associated with a physical activity and an average or baseline measurement associated with the physical activity, as will be discussed in further detail below.

Returning now to FIG. 3, in one embodiment, once the defined change in altitude range and change in motion range are correlated with the physical activity at 310, process flow proceeds to 312. In one embodiment, at 312, current altitude and/or motion data is received from one or more devices associated with the user.

As discussed above, in various embodiments, a user device may be any type of device that is portable and capable of providing altitude and/or motion data, or any type of device that is portable and capable of providing raw data that can be used to calculate altitude and/or motion data, including, but not limited to, a cellular device, a handheld device, a wearable device, an implantable device, a sensor device, an accelerometer device, a motion detection device, or any other type of device currently known to those of skill in the art, or any other type of device that may be developed after the time of filing.

In one embodiment, the user device is programmed to continually collect and transmit altitude and/or motion data in real-time as the user goes about their daily activities. In one embodiment, the user device is programmed to collect and transmit altitude and/or motion data at predetermined intervals, such as once per minute, or once every 10 seconds. In some embodiments the user can determine the desired timing of data collection by entering configuration data through a user interface of the application. In some embodiments, the user may choose specific moments to collect and transmit data, or may choose when to start data collection and when to stop data collection, for example, by pushing a button on the device, toggling a switch on the device, or issuing a voice command to the device. If the device incorporates a touch screen, the user may also perform a variety of touch-based gestures to issue data collection and transmission commands to the device.

In some embodiments, the application is provided to the user on the user device, such as through a display screen of a smart phone or smart watch. In other embodiments, the user device is separate from the computing system that provides the application user interface, and the device settings may be configured through the application user interface on any type of computing system, including, but not limited to, a desktop computing system application, a mobile computing system application, a virtual reality computing system application, an application provided by an Internet of Things (IoT) device, or any combination thereof. Further, in various embodiments, the user interface may include any combination of a graphical user interface, an audio-based user interface, a touch-based user interface, or any other type of user interface currently known to those of skill in the art, or any other type of user interface that may be developed after the time of filing.

Returning briefly to FIG. 1C, in one embodiment the current device altitude and/or motion data 104 is received from user device 102 of user 101 by user device data acquisition module 121. In various embodiments, the current device altitude and/or motion data 104 may be stored in a portion of user database 112 that is associated with user 101 for further analysis and processing.

Returning now to FIG. 3, in one embodiment, once current altitude and/or motion data is received from one or more devices associated with the user of the application at 312, process follow proceeds to 314. In one embodiment, at 314, the current altitude data is analyzed to identify altitude changes in the defined change in altitude range associated with the physical activity being monitored, and/or the current motion data is analyzed to identify motion changes in the defined change in motion range associated with the physical activity being monitored.

As discussed above, in various embodiments, the current altitude and/or motion data is collected, processed, and analyzed to determine whether a change in altitude and/or change in motion is currently occurring or has recently occurred. Upon a determination that a change in altitude and/or change in motion is currently occurring or has recently occurred, current change in altitude data may be generated representing one or more values associated with the altitude change, and/or current change in motion data may be generated representing one or more values associated with the motion change. The current change in altitude data may then be compared with the change in altitude range that was previously defined and correlated with the physical activity being monitored to determine whether the current change in altitude falls within the change in altitude range for the physical activity being monitored. Likewise, the current change in motion data may be compared with the change in motion range that was previously defined and correlated with the physical activity being monitored to determine whether the current change in motion falls within the change in motion range for the physical activity being monitored.

Returning briefly again to FIG. 1C, in one embodiment current physical activity analysis module 122 analyzes the current device altitude and/or motion data 104 to generate current change in altitude data, which may then be compared with change in altitude range data 154 to determine whether the current change in altitude falls within the change in altitude range for the physical activity being monitored. Likewise, current physical activity analysis module 122 may analyze the current device altitude and/or motion data 104 to generate current change in motion data, which may then be compared with change in motion range data 156 to determine whether the current change in motion falls within the change in motion range for the physical activity being monitored.

Returning to FIG. 3, in one embodiment, at 314, once the current altitude data is analyzed to identify altitude changes in the defined change in altitude range associated with the physical activity being monitored, and/or the current motion data is analyzed to identify motion changes in the defined change in motion range associated with the physical activity being monitored, process flow proceeds to 316. In one embodiment, at 316, each instance of a current altitude and/or motion change that has been identified as falling with the defined change in altitude and/or motion range is labeled as an occurrence of the physical activity. As already discussed above, in some situations, there may be significant overlap between a change in altitude and/or motion range of one physical activity and a change in altitude and/or motion range of a different physical activity. In situations like these, the addition of location data may serve to disambiguate one physical activity from another.

In one embodiment, once any ambiguities have been resolved and one or more occurrences of the physical activity have been identified and labeled at 316, process flow proceeds to 318. In one embodiment, at 318, the current number of times the physical activity is performed by the user in the defined timeframe is determined.

As discussed above, at operation 306 an average number of occurrences of the physical activity being monitored was defined for a set of people in a defined timeframe. Any suitable timeframe may have been selected, such that analysis of the average physical activity data is able to yield meaningful results. As one illustrative example, if the physical activity being monitored is sitting, the previously defined average physical activity data may include data indicating the average number of times per day that people with the same medical condition as the user changed from a standing position to a sitting position over the course of the past month. Thus, the timeframe used to calculate average data, i.e., per day, would be utilized at operation 318, and the current number of times the user changed from a standing position to a sitting position would be calculated for the current day. As also noted above, in addition to the number of times that a physical activity is performed, additional metrics may also be evaluated at operation 318, such as, but not limited to, the speed, velocity, and/or acceleration at which the user performed the physical activity, and the length of time that the user spent engaging in the physical activity.

Returning briefly again to FIG. 1C, in one embodiment, current physical activity analysis module 122 performs the above described processing and analysis, and generates current physical activity data 140, which may be stored in the portion of user database 112 associated with user 101. Current physical activity analysis module 122 may generate current physical activity count data 142 based on the number of times that a physical activity is performed by user 101, as well as current physical activity speed data 144, based on the speed, velocity, and/or acceleration at which the user 101 performed the physical activity. In various other embodiments, additional data, such as, but not limited to, current physical activity length data may be generated, based on the length of time user 101 spent engaging in the physical activity, and this physical activity length data may also be stored as part of current physical activity data 140.

Returning now to FIG. 3, in one embodiment, once the current number of times the physical activity is performed by the user is determined for the defined timeframe at 318, process flow proceeds to 320. In one embodiment, at 320, the current number of times the physical activity was performed by the user in the defined timeframe is compared with the average number of occurrences of the physical activity in the defined timeframe for a set of people.

As noted above, average physical activity data that was previously determined may include a variety of data related to one or more physical activities being monitored. At 320, the average data for the current physical activity being monitored may be retrieved from a portion of the physical activity database associated with a particular set of people, for comparison with the current physical activity data for the user and current physical activity being monitored. As also discussed above, a set of people may include sets of people such as, but not limited to: a set of average people; a set of people with one or more of the same medical conditions; a set of people with one or more substantially similar medical conditions; a set of people with one or more of the same physical and/or mental symptoms; a set of people with one or more substantially similar physical and/or mental symptoms; a set of people taking one or more of the same medications; a set of people taking one or more substantially similar medications; a set of people that are in the same age range; a set of people that are the same sex; and a set of people that are the same ethnicity.

Returning again to FIG. 1C, for example, in one embodiment, current physical activity count data 142 may be compared to average physical activity count data 166, which represents data associated with a particular set of people and the physical activity being monitored. Additionally, current physical activity speed data 144 may be compared to average physical activity speed data 168, which represents data associated with a particular set of people and the physical activity being monitored. In this example, the comparison may yield that there is no difference between the current physical activity data 140 and the average physical activity data 164, that there is a small difference between the current physical activity data 140 and the average physical activity data 164, or that there is a large difference between the current physical activity data 140 and the average physical activity data 164. As discussed above, in order to define what constitutes a "small" difference and a "large" difference, one or more activity thresholds, represented by activity threshold data 158, may first need to be defined. In the illustrative embodiment of FIG. 1C, the above described comparison is performed by physical activity comparator module 123.

Returning now to FIG. 3, in one embodiment, once the current number of times the physical activity was performed by the user in the defined timeframe is compared with the average number of occurrences of the physical activity in the defined timeframe for a set of people at 320, process flow proceeds to 322. In one embodiment, at 322, if the result of the comparison at 320 indicates that the current number of times the physical activity is performed by the user in the defined timeframe differs from the average number of occurrences of the physical activity in the defined timeframe for a set of people by a threshold amount, one or more actions are taken.

As noted above, in one embodiment, one or more activity thresholds are defined, such that when the user's current physical activity data varies from the average physical activity data, appropriate actions can be taken. In one embodiment, the one or more activity thresholds are represented by activity threshold data, which may be stored as part of a physical activity database. In one embodiment, an activity threshold represents a maximum allowable variation between a user's current physical activity data and the average physical activity data. In various embodiments, the one or more activity thresholds may be defined in various ways, such as, but not limited to, through application configuration options, or use of a predetermined standard.

For example, in one embodiment, after definition of average physical activity data for a set of people, it may be determined that the average physical activity count, associated with a set of people with the same medical condition as the user, for the activity being monitored, is 5 times per day. It may be decided by specialists, or other experts in the field of use, that a variance of 3 counts per day is relatively common, and as such, if the current physical activity data for this user indicated a physical activity count of 8 times per day or 2 times per day with respect to the physical activity being monitored, this would not raise concerns. However, if the current physical activity data for this user indicated a physical activity count of 10 times per day or 0 times per day with respect to the physical activity being monitored, this would raise concerns, and further action might be deemed appropriate, as will be discussed in further detail below. It should be noted again here, that the foregoing examples are given for illustrative purposes only, and are not intended to limit the scope of the invention as disclosed herein and as claimed below.

As already noted above, in various embodiments, multiple averages may be defined during the definition of the average physical activity data, and as such, it follows from the preceding discussion that there could potentially be a different activity threshold associated with each of the individual averages that form the average physical activity data.

In one embodiment, if the difference between the current physical activity data and the average physical activity data is greater than the activity threshold corresponding to the average, it may be determined that this is indicative of a change or anomaly in the physical and/or psychological state of the user, and thus one or more predictions regarding the user's current physical and/or mental state may be made. Upon identifying the current user's physical and/or mental state and/or identifying changes or anomalies in the current user's physical and/or mental state, one or more actions may be taken.

As discussed above, in various embodiments, if an anomaly is detected in the physical and/or psychological state of the user, several types of actions may be appropriate specifically when dealing with users who are patients diagnosed with a medical condition, and the actions to be taken may be determined based on the severity of any identified anomaly. For example, if a minor anomaly is detected in the physical and/or psychological state of the user, actions might be taken such as, but not limited to: asking the user for input and/or response data; alerting the user; providing suggestions or other information to the user; making notes in, adding data to, or highlighting the user's electronic file. On the other hand, if a major anomaly is detected in the physical and/or psychological state of the user, actions might be taken such as, but not limited to: alerting one or more of the user's mental health or medical professionals; making a specialist referral; recommending support contacts to the user; prescribing additional appointments, treatments, actions, or medications; calling emergency response or intervention professionals; notifying emergency contacts, relatives, or caregivers, etc.

In various embodiments, actions that may be taken further include delivering tailored content to the user through a user interface of the application. As already noted above, the application may be provided to the user on the same user device that is used to collect the altitude and/or motion data, however the application may instead, or in addition, be provided to the user on any type of computing system. In one embodiment, a user of a digital therapeutics application is provided with a user interface, and is also provided with content-based information through the user interface. Content that may be provided includes content such as, but not limited to, information related to the user's medical history, current or potential medical care providers, medical conditions, medications, nutritional supplements, advice or suggestions regarding diet and/or exercise, or any other type of information that may be considered relevant to the user.

In addition to the types of content-based information discussed above, another type of data that may be presented to the user is user experience data. Examples of user experience data include, but are not limited to, the colors and fonts used to present the content-based information to a user, the various shapes of the graphical user interface elements, the layout or ordering of the content-based information presented to a user, and/or the sound effects, music, or other audio elements that may accompany the presentation of or interaction with the content-based information.

As noted above, the actions to be taken may be determined based on the severity of any identified anomaly. In the case of tailoring content to the user, if the anomaly is minor, then actions might be taken to make slight adjustments to the information content data and/or the user experience data that is presented to the user. On the other hand, if the anomaly is severe, then actions might be taken to make extreme adjustments to the information content data and/or the user experience data that is presented to the user. In one embodiment, adjustments to the information content data may include adjustments such as, but not limited to, providing textual content that uses gentler language, providing audio content that includes quieter, more relaxing voices, sounds, or music, or providing image/video content that is less realistic or less graphic. Adjustments to the user experience data may include adjustments such as, but not limited to, changing the colors, fonts, shapes, presentation, and/or layout of the information content data presented to the user.

In one embodiment, in addition to determining content to provide to the user based on the identification of anomalous physical activity data, the timing of notifications, alerts, or other content delivered to the user can also be determined based on the identification of anomalous physical activity data. For example, if the physical activity data indicates that a user is using the bathroom more frequently than usual, application usage reminders, therapeutic content, and other types of notifications, alerts, or content can be delivered at specific and appropriate times. The physical activity data can also be analyzed and utilized to generate or adjust one or more content delivery schedules that are tailored specifically to the user's habits and routines.

Returning again to FIG. 1C, in one embodiment, once physical activity comparator module 123 has compared user 101's current physical activity data 140 with average physical activity data 164 to determine whether the difference between user 101's current physical activity data 140 and the average physical activity data 164 is greater than the threshold in activity threshold data 158 that corresponds to the physical activity being monitored, the resulting data is analyzed and processed by action determination module 124. In one embodiment, action determination module 124 determines one or more actions that should be taken, based on the variety of factors discussed above. Upon determination of one or more actions to be taken, action execution module 125 proceeds to take any steps necessary to execute the one or more actions. Depending on the actions determined by action determination module 124, action execution module 125 may further utilize content and user experience generation module 126, which handles the generation or modification of information content data 160 and user experience data 162 based on user physical activity data 114. The information content data 160 and user experience data 162 may then be provided through user interface 130 to user device 102 associated with user 101 or to user computing system 134 associated with user 101 over the one or more communications networks 136.

In one embodiment, once one or more actions are taken at 322, process flow proceeds to END 324 and the process 300 for remotely identifying and monitoring changes or anomalies in the physical and/or psychological state of an application user using baseline physical activity data is exited to await new data and/or instructions.

III. Methods and Systems Using Machine Learning

Figure 4:
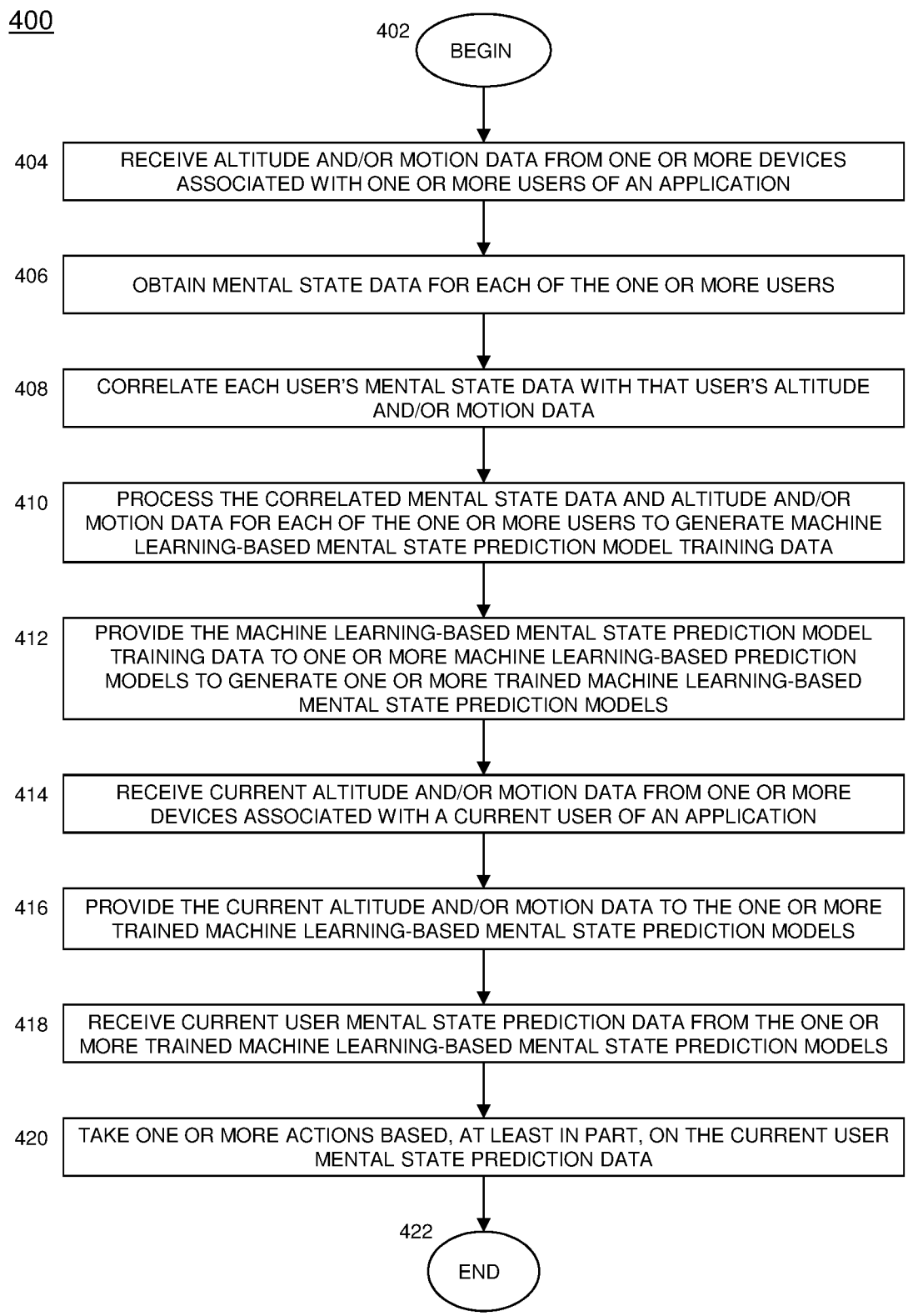
FIG. 4 is a flow chart of a process for remotely identifying and monitoring anomalies in the physical and/or psychological state of an application user using device altitude data and/or motion data and one or more machine learning models, in accordance with one embodiment.

In some embodiments, the physical and/or psychological state of an application user is identified and monitored using machine learning methods. Together FIGS. 1A, 1D, and 4 depict one example of a method and system for remotely identifying and monitoring anomalies in the physical and/or psychological state of an application user using device altitude data and/or motion data and one or more machine learning models.

Figure 1D:
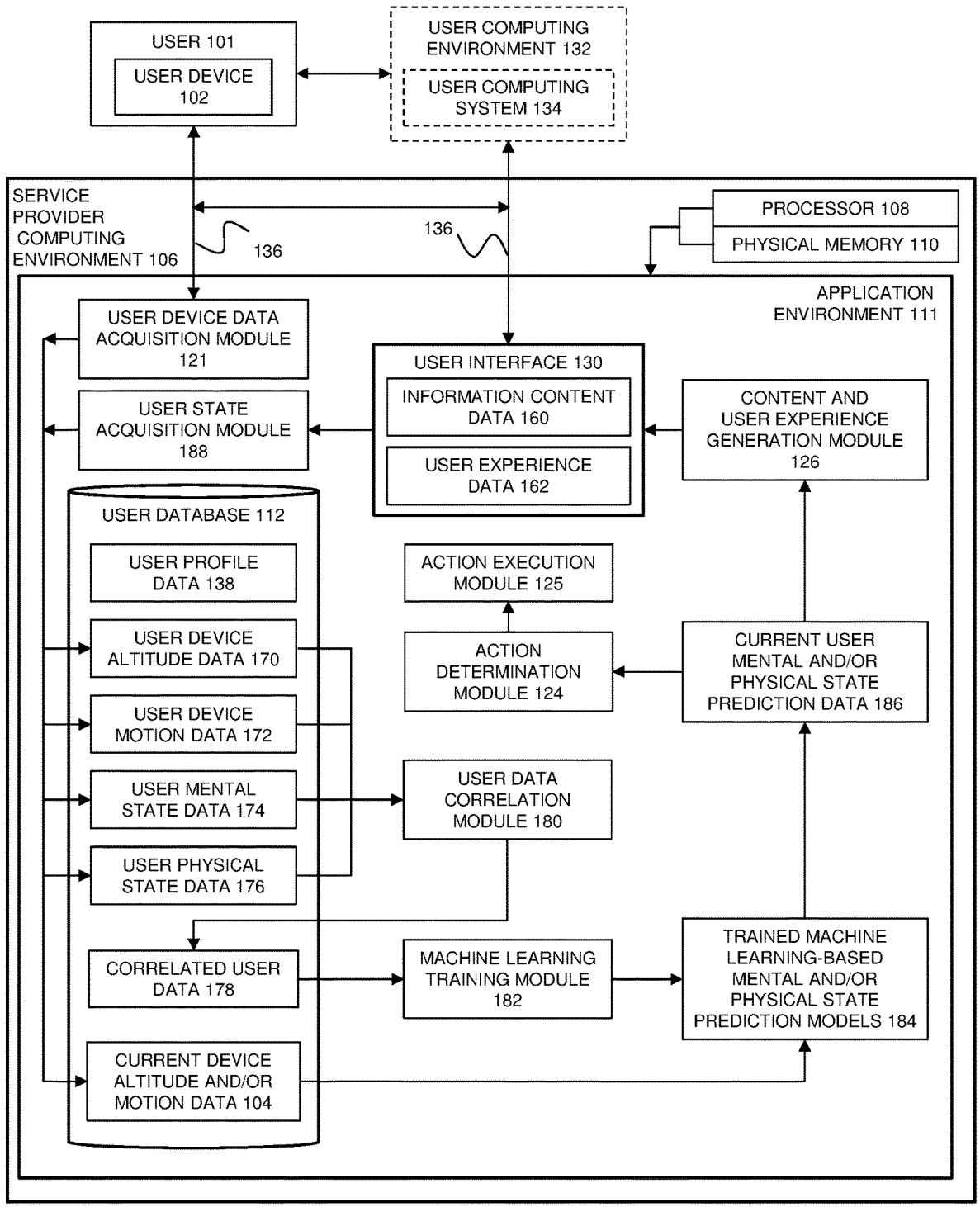
FIG. 1D is a block diagram of a production environment for remotely identifying and monitoring anomalies in the physical and/or psychological state of an application user using device altitude data and machine learning models, in accordance with one embodiment.

FIG. 1D is a block diagram of a production environment 100D for remotely identifying and monitoring anomalies in the physical and/or psychological state of an application user using device altitude data and/or motion data and one or more machine learning models, in accordance with one embodiment.

Referring to FIGS. 1A and 1D together, in one embodiment, production environment 100D includes user 101, user device 102, service provider computing environment 106 and, optionally, user computing environment 132 and user computing system 134. Service provider computing environment 106 includes application environment 111, processor 108, and physical memory 110. Processor 108 and physical memory 110 coordinate the operation and interaction of the data and data processing modules associated with application environment 111.

In one embodiment, application environment 111 includes user database 112. User database 112 further includes user profile data 138, current device altitude and/or motion data 104, user device altitude data 170, user device motion data 172, user mental state data 174, user physical state data 176, and correlated user data 178, each of which will be discussed in further detail below.

In one embodiment application environment 111 also includes several process modules, such as, but not limited to, user device data acquisition module 121, user state acquisition module 188, user data correlation module 180, action determination module 124, action execution module 125, and content and user experience generation module 126. In one embodiment, application environment 111 further includes machine learning training module 182, trained machine learning-based mental and/or physical state prediction models 184, and current user mental and/or physical state prediction data 186, each of which will be discussed in further detail below.

In one embodiment, application environment 111 also includes user interface 130, which may be utilized to provide information content data 160 and/or user experience data 162 to user device 102 associated with user 101 and/or to user computing system 134 associated with user 101, over one or more communications networks 136, each of which will be discussed in further detail below.

FIG. 4 is a flow chart of a process for remotely identifying and monitoring anomalies in the physical and/or psychological state of an application user using device altitude data and/or motion data and one or more machine learning models, in accordance with one embodiment.

In one embodiment, process 400 begins at BEGIN 402 and process flow proceeds to 404. In one embodiment, at 404, altitude and/or motion data is received from one or more devices associated with one or more users of an application.

As discussed above, in various embodiments, a device associated with a user may be any type of device that is portable and capable of providing altitude and/or motion data, or any type of device that is portable and capable of providing raw data that can be used to calculate altitude and/or motion data, including, but not limited to, a cellular device, a handheld device, a wearable device, an implantable device, a sensor device, an accelerometer device, a motion detection device, or any other type of device currently known to those of skill in the art, or any other type of device that may be developed after the time of filing.

In one embodiment, a user device is programmed to continually collect and transmit altitude and/or motion data in real-time as the user associated with the device goes about their daily activities. In one embodiment, the user device is programmed to collect and transmit altitude and/or motion data at predetermined intervals, such as once per minute, or once every 10 seconds. In some embodiments a user can determine the desired timing of data collection by entering configuration data through a user interface of the application. In some embodiments, a user may choose specific moments to collect and transmit data, or may choose when to start data collection and when to stop data collection, for example, by pushing a button on the device, toggling a switch on the device, or issuing a voice command to the device. If the device associated with a user incorporates a touch screen, a user may also perform a variety of touch-based gestures to issue data collection and transmission commands to the device.

In some embodiments, the application is provided to a user on the user device, such as through a display screen of a smart phone or smart watch. In other embodiments, the user device is separate from the computing system that provides the application user interface, and the device settings may be configured through the application user interface on any type of computing system, including, but not limited to, a desktop computing system application, a mobile computing system application, a virtual reality computing system application, an application provided by an Internet of Things (IoT) device, or any combination thereof. Further, in various embodiments, the user interface may include any combination of a graphical user interface, an audio-based user interface, a touch-based user interface, or any other type of user interface currently known to those of skill in the art, or any other type of user interface that may be developed after the time of filing.

Returning briefly to FIG. 1D, in one embodiment user device altitude data 170 and/or user device motion data 172 is received from one or more user devices associated with a variety of users by user device data acquisition module 121. In various embodiments, the user device altitude data 170 and/or user device motion data 172 includes data retrieved from a wide variety of users, and may be stored in a portion of user database 112 that is associated with multiple users for further analysis and processing.

Returning now to FIG. 4, in one embodiment, once altitude and/or motion data is received from one or more devices associated with one or more users of an application at 404, process follow proceeds to 406. In one embodiment, at 406, mental state data for each of the one or more users is obtained.

In various embodiments mental state data includes data related to the type and intensity of psychological sensations that a user may be experiencing, such as, but not limited to, calmness, happiness, euphoria, anxiety, panic, fear, depression, anger, and aggression. In the specific embodiment where the user is a patient who has been diagnosed with a disease, mental state data may also include data such as one or more indicators of perceived pain and one or more indicators of the level of stress the patient may be experiencing due to their disease.

In one embodiment, user mental state data is obtained from each of the one or more users by interviewing each of the one or more users before, after, or during acquisition of the user's device altitude and/or motion data at 404. In some embodiments, at 406, user mental state data is obtained by consulting with a third party, such as a medical professional associated with the user, before or after acquisition of the user's device altitude and/or motion data at 404. In some embodiments, at 406, user mental state data is obtained from data in one or more files associated with a user indicating none or more events occurring before or after acquisition of the user's device altitude and/or motion data at 404. Such events may include, but are not limited to, a change in diagnosis of the user's health, a change in medication, a change in the user's personal life, or any other event indicating the mental state of the user at or near the time the user's device altitude and/or motion data is acquired at 404.

Returning briefly to FIG. 1D, in one embodiment, user state acquisition module 188 receives the mental state data for one or more of the users through user interface 130 of application environment 111. The mental state data for the one or more users may then be stored in user database 112 as user mental state data 174.

Returning now to FIG. 4, in one embodiment, once mental state data for each of the one or more users is obtained at 406, process flow proceeds to 408. In one embodiment, at 408, each user's mental state data is correlated with that user's altitude and/or motion data.

Returning now to FIG. 1D, in one embodiment, the mental state data collected for each of the one or more users is stored in user database 112 as user mental state data 174. User data correlation module 180 is then responsible for correlating the data in user device altitude data 170 and/or the data in user device motion data 172 associated with each of the one or more users with the data in user mental state data 174 associated with each of the one or more users. In one embodiment, once one or more user's user device altitude data 170 and/or user device motion data 172 have been correlated with that user's mental state data 174, user data correlation module 180 may store the correlated user data 178 in user database 112 for further analysis and processing.

Returning to FIG. 4, in one embodiment, once each user's mental state data is correlated with that user's altitude and/or motion data at 408, process flow proceeds to 410. In one embodiment, at 410, the correlated mental state data and altitude and/or motion data for each of the one or more users is processed to generate machine learning-based mental state prediction model training data.

Returning now to FIG. 1D, in various embodiments, and largely depending on the machine learning-based models used, the user device altitude data 170, user device motion data 172, and/or the user mental state data 174, which has been correlated by user data correlation module 180 to generate correlated user data 178, is processed by machine learning training module 182, using various methods known in the machine learning arts, to identify elements and vectorize the user device altitude data 170, user device motion data 172 and/or the user mental state data 174. As a specific illustrative example, in a case where the machine leaning based model is a supervised model, the user device altitude data 170, the user device motion data 172, and the user mental state data 174 can be analyzed and processed by machine learning training module 182 to identify individual elements found to be indicative of a user's mental state. These individual elements are then used to create user device altitude and/or motion vectors in multidimensional space which are, in turn, used as input data for training one or more machine learning-based models, such as trained machine learning-based mental and/or physical state prediction models 184.

In one embodiment, the user device altitude data 170 and/or user device motion data 172 is first processed to generate physical activity data, such as, but not limited to, physical activity identification data, physical activity count data representing the number of times a physical activity is performed by a user in a defined timeframe, physical activity speed data representing the speed, velocity, and/or acceleration at which a physical activity is performed by a user, and/or physical activity length data representing the length of time that a user spends engaging in a physical activity. In one embodiment, the generated physical activity data is then correlated with the mental state data and used to generate the machine learning-based mental state prediction model training data.

Returning to FIG. 4, in one embodiment, once the correlated mental state data and altitude and/or motion data for each of the one or more users is processed to generate machine learning-based mental state prediction model training data at 410, process flow proceeds to 412. In one embodiment, at 412, the machine learning-based mental state prediction model training data is provided to one or more machine learning-based prediction models to generate one or more trained machine learning-based mental state prediction models.

In one embodiment, the machine learning-based mental state prediction model training data is provided to one or more machine learning-based prediction models, and the mental state data for a user that correlates with the user device altitude and/or motion data vectors associated with that user is then used as a label for the resulting vector. In various embodiments, this process is repeated for the user device altitude and/or motion data and mental state data received from each of the one or more users, such that multiple, often millions, of correlated pairs of user altitude and/or motion data vectors and user mental state data vectors are used to train one or more machine learning based models. Consequently, this process results in the creation of one or more trained machine learning-based mental state prediction models.

Those of skill in the art will readily recognize that there are many different types of machine learning-based models known in the art, and as such, it should be noted that the specific illustrative example of a supervised machine learning based model discussed above should not be construed as limiting the embodiments set forth herein. For instance, in various embodiments, the one or more machine learning-based models can be one or more of: supervised machine learning-based models; semi supervised machine learning-based models; unsupervised machine learning-based models; classification machine learning-based models; logistical regression machine learning-based models; neural network machine learning-based models; deep learning machine learning-based models; and/or any other machine learning based models discussed herein, known at the time of filing, or as developed/made available after the time of filing.

In one embodiment, once the machine learning-based mental state prediction model training data is provided to one or more machine learning-based prediction models to generate one or more trained machine learning-based mental state prediction models at 412, process flow proceeds to 414.

In one embodiment, at 414, current altitude and/or motion data from one or more devices associated with a current user of an application is received.

As already discussed above, in various embodiments, a user device may be any type of device that is portable and capable of providing altitude and/or motion data, or any type of device that is portable and capable of providing raw data that can be used to calculate altitude and/or motion data, including, but not limited to, a cellular device, a handheld device, a wearable device, an implantable device, a sensor device, an accelerometer device, a motion detection device, or any other type of device currently known to those of skill in the art, or any other type of device that may be developed after the time of filing.

In one embodiment, the user device is programmed to continually collect and transmit altitude and/or motion data in real-time as the user goes about their daily activities. In one embodiment, the user device is programmed to collect and transmit altitude and/or motion data at predetermined intervals, such as once per minute, or once every 10 seconds. In some embodiments the user can determine the desired timing of data collection by entering configuration data through a user interface of the application. In some embodiments, the user may choose specific moments to collect and transmit data, or may choose when to start data collection and when to stop data collection, for example, by pushing a button on the device, toggling a switch on the device, or issuing a voice command to the device. If the device incorporates a touch screen, the user may also perform a variety of touch-based gestures to issue data collection and transmission commands to the device.

In some embodiments, the application is provided to the user on the user device, such as through a display screen of a smart phone or smart watch. In other embodiments, the user device is separate from the computing system that provides the application user interface, and the device settings may be configured through the application user interface on any type of computing system, including, but not limited to, a desktop computing system application, a mobile computing system application, a virtual reality computing system application, an application provided by an Internet of Things (IoT) device, or any combination thereof. Further, in various embodiments, the user interface may include any combination of a graphical user interface, an audio-based user interface, a touch-based user interface, or any other type of user interface currently known to those of skill in the art, or any other type of user interface that may be developed after the time of filing.

Returning briefly to FIG. 1D, in one embodiment the current device altitude and/or motion data 104 is received from user device 102 associated with user 101 by user device data acquisition module 121. In various embodiments, the current device altitude and/or motion data 104 may be stored in a portion of user database 112 that is associated with user 101 for further analysis and processing.

Returning to FIG. 4, in one embodiment, once current altitude and/or motion data from one or more devices associated with a current user of an application is received at 414, process flow proceeds to 416. In one embodiment, at 416, the current altitude and/or motion data is provided to the one or more trained machine learning-based mental state prediction models.

In one embodiment, the current altitude and/or motion data received at 414 is vectorized to generate one or more current device altitude and/or motion data vectors. The one or more current device altitude and/or motion data vectors associated with the current user are then provided as input data to the one or more trained machine learning-based mental state prediction models. The current device altitude and/or motion vector data is then processed to find a distance between the one or more current device altitude and/or motion data vectors and one or more previously labeled user device altitude and/or motion vectors, where the previously labeled user device altitude and/or motion vectors are vectors with known associated user mental state data. In one embodiment, one or more probability scores are determined based on a calculated distance between the current user device altitude and/or motion vector data and the previously labeled user device altitude and/or motion vector data. Upon determination that the one or more current user device altitude and/or motion vectors correlate to a user mental state associated with the previously labeled user device altitude and/or motion vectors, current user mental state prediction data is generated. In one embodiment, the current user mental state prediction data comprises one or more probability scores, which indicate the probability that the current user is in one or more particular mental states.

In one embodiment, the current altitude and/or motion data is first processed to generate physical activity data, such as, but not limited to, physical activity identification data, physical activity count data representing the number of times a physical activity is performed by a user in a defined timeframe, physical activity speed data representing the speed, velocity, and/or acceleration at which a physical activity is performed by a user, and/or physical activity length data representing the length of time that a user spends engaging in a physical activity. In one embodiment, the generated physical activity data is then vectorized and provided as input data to the one or more trained machine learning-based mental state prediction models.

In one embodiment, once the current altitude and/or motion data is provided to the one or more trained machine learning-based mental state prediction models at 416, process flow proceeds to 418. In one embodiment, at 418, current user mental state prediction data is received from the one or more trained machine learning-based mental state prediction models.

Returning again to FIG. 1D, as noted above, in one embodiment, the current user mental state prediction data received from the one or more trained machine learning-based mental state prediction models, which are part of trained machine learning-based mental and/or physical state prediction models 184, comprises one or more probability scores, which indicate the probability that the current user is in one or more particular mental states. The current user mental state prediction data is then aggregated with any current user physical state prediction data to generate current user mental and/or physical state prediction data 186.

Returning to FIG. 4, in one embodiment, once current user mental state prediction data is received from the one or more trained machine learning-based mental state prediction models at 418, process flow proceeds to 420. In one embodiment, at 420 one or more actions are taken, based, at least in part, on the current user mental state prediction data. The one or more actions taken will be discussed in further detail, in the discussion of FIG. 5 below.

In one embodiment, once one or more actions are taken at 420, process flow proceeds to END 422 and the process 400 for remotely identifying and monitoring anomalies in the psychological state of an application user using device altitude data and machine learning models is exited to await new data and/or instructions.

Figure 5:
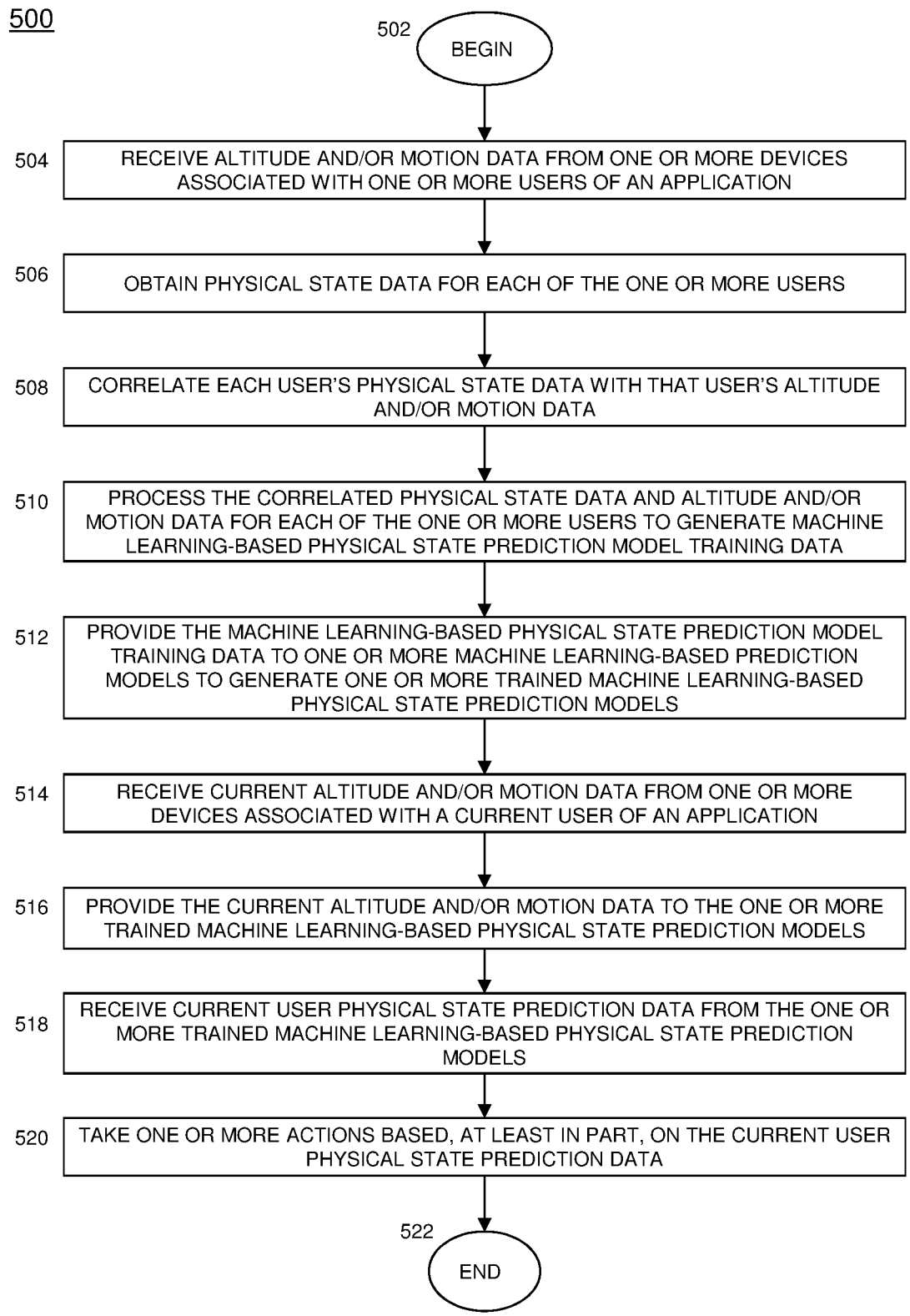
FIG. 5 is a is a flow chart of a process for remotely identifying and monitoring anomalies in the physical and/or psychological state of an application user using device altitude data and/or motion data and one or more machine learning models, in accordance with one embodiment.

Together FIGS. 1A, 1D, and 5 depict another example of a method and system for remotely identifying and monitoring anomalies in the physical and/or psychological state of an application user using device altitude data and/or motion data and one or more machine learning models.

FIG. 5 is a flow chart of a process for remotely identifying and monitoring anomalies in the physical and/or psychological state of an application user using device altitude data and/or motion data and one or more machine learning models, in accordance with one embodiment.

In one embodiment, process 500 begins at BEGIN 502 and process flow proceeds to 504. In one embodiment, at 504, altitude and/or motion data is received from one or more devices associated with one or more users of an application.

As discussed above, in various embodiments, a device associated with a user may be any type of device that is portable and capable of providing altitude and/or motion data, or any type of device that is portable and capable of providing raw data that can be used to calculate altitude and/or motion data, including, but not limited to, a cellular device, a handheld device, a wearable device, an implantable device, a sensor device, an accelerometer device, a motion detection device, or any other type of device currently known to those of skill in the art, or any other type of device that may be developed after the time of filing.

In one embodiment, a user device is programmed to continually collect and transmit altitude and/or motion data in real-time as the user associated with the device goes about their daily activities. In one embodiment, the user device is programmed to collect and transmit altitude and/or motion data at predetermined intervals, such as once per minute, or once every 10 seconds. In some embodiments a user can determine the desired timing of data collection by entering configuration data through a user interface of the application. In some embodiments, a user may choose specific moments to collect and transmit data, or may choose when to start data collection and when to stop data collection, for example, by pushing a button on the device, toggling a switch on the device, or issuing a voice command to the device. If the device associated with a user incorporates a touch screen, a user may also perform a variety of touch-based gestures to issue data collection and transmission commands to the device.

In some embodiments, the application is provided to a user on the user device, such as through a display screen of a smart phone or smart watch. In other embodiments, the user device is separate from the computing system that provides the application user interface, and the device settings may be configured through the application user interface on any type of computing system, including, but not limited to, a desktop computing system application, a mobile computing system application, a virtual reality computing system application, an application provided by an Internet of Things (IoT) device, or any combination thereof. Further, in various embodiments, the user interface may include any combination of a graphical user interface, an audio-based user interface, a touch-based user interface, or any other type of user interface currently known to those of skill in the art, or any other type of user interface that may be developed after the time of filing.

Returning briefly to FIG. 1D, in one embodiment user device altitude data 170 and/or user device motion data 172 is received from one or more user devices associated with a variety of users by user device data acquisition module 121. In various embodiments, the user device altitude data 170 and/or user device motion data 172 includes data retrieved from a wide variety of users, and may be stored in a portion of user database 112 that is associated with multiple users for further analysis and processing.

Returning now to FIG. 5, in one embodiment, once altitude and/or motion data is received from one or more devices associated with one or more users of an application at 504, process follow proceeds to 506. In one embodiment, at 506, physical state data for each of the one or more users is obtained.

In one embodiment, user physical state data is obtained from each of the one or more users by interviewing each of the one or more users before, after, or during acquisition of the user's device altitude and/or motion data at 504. In some embodiments, at 506, user physical state data is obtained by consulting with a third party, such as a medical professional associated with the user, before or after acquisition of the user's device altitude and/or motion data at 504. In some embodiments, at 506, user physical state data is obtained from data in one or more files associated with a user indicating none or more events occurring before or after acquisition of the user's device altitude and/or motion data at 504. Such events may include, but are not limited to, a change in diagnosis of the user's health, a change in medication, a change in the user's personal life, or any other event indicating the physical state of the user at or near the time the user's device altitude and/or motion data is acquired at 504.

Returning briefly to FIG. 1D, in one embodiment, user state acquisition module 188 receives the physical state data for one or more of the users through user interface 130 of application environment 111. The physical state data for the one or more users may then be stored in user database 112 as user physical state data 176.

Returning now to FIG. 5, in one embodiment, once physical state data for each of the one or more users is obtained at 506, process flow proceeds to 508. In one embodiment, at 508, each user's physical state data is correlated with that user's altitude and/or motion data.

Returning now to FIG. 1D, in one embodiment, the physical state data collected for each of the one or more users is stored in user database 112 as user physical state data 176. User data correlation module 180 is then responsible for correlating the data in user device altitude data 170 and/or the data in user device motion data 172 associated with each of the one or more users with the data in user physical state data 176 associated with each of the one or more users. In one embodiment, once one or more user's user device altitude data 170 and/or user device motion data 172 have been correlated with that user's physical state data 176, user data correlation module 180 may store the correlated user data 178 in user database 112 for further analysis and processing.

Returning to FIG. 5, in one embodiment, once each user's physical state data is correlated with that user's altitude and/or motion data at 508, process flow proceeds to 510. In one embodiment, at 510, the correlated physical state data and altitude and/or motion data for each of the one or more users is processed to generate machine learning-based physical state prediction model training data.

Returning now to FIG. 1D, in various embodiments, and largely depending on the machine learning-based models used, the user device altitude data 170, user device motion data 172, and/or the user physical state data 176, which has been correlated by user data correlation module 180 to generate correlated user data 178, is processed by machine learning training module 182, using various methods known in the machine learning arts, to identify elements and vectorize the user device altitude data 170, user device motion data 172 and/or the user physical state data 176. As a specific illustrative example, in a case where the machine leaning based model is a supervised model, the user device altitude data 170, the user device motion data 172, and the user physical state data 176 can be analyzed and processed by machine learning training module 182 to identify individual elements found to be indicative of a user's physical state. These individual elements are then used to create user device altitude and/or motion vectors in multidimensional space which are, in turn, used as input data for training one or more machine learning-based models, such as trained machine learning-based mental and/or physical state prediction models 184.

In one embodiment, the user device altitude data 170 and/or user device motion data 172 is first processed to generate physical activity data, such as, but not limited to, physical activity identification data, physical activity count data representing the number of times a physical activity is performed by a user in a defined timeframe, physical activity speed data representing the speed, velocity, and/or acceleration at which a physical activity is performed by a user, and/or physical activity length data representing the length of time that a user spends engaging in a physical activity. In one embodiment, the generated physical activity data is then correlated with the physical state data and used to generate the machine learning-based physical state prediction model training data.

Returning to FIG. 5, in one embodiment, once the correlated physical state data and altitude and/or motion data for each of the one or more users is processed to generate machine learning-based physical state prediction model training data at 510, process flow proceeds to 512. In one embodiment, at 512, the machine learning-based physical state prediction model training data is provided to one or more machine learning-based prediction models to generate one or more trained machine learning-based physical state prediction models.

In one embodiment, the machine learning-based physical state prediction model training data is provided to one or more machine learning-based prediction models, and the physical state data for a user that correlates with the user device altitude and/or motion data vectors associated with that user is then used as a label for the resulting vector. In various embodiments, this process is repeated for the user device altitude and/or motion data and physical state data received from each of the one or more users, such that multiple, often millions, of correlated pairs of user altitude and/or motion data vectors and user physical state data vectors are used to train one or more machine learning based models. Consequently, this process results in the creation of one or more trained machine learning-based physical state prediction models.

Those of skill in the art will readily recognize that there are many different types of machine learning-based models known in the art, and as such, it should be noted that the specific illustrative example of a supervised machine learning based model discussed above should not be construed as limiting the embodiments set forth herein. For instance, in various embodiments, the one or more machine learning-based models can be one or more of: supervised machine learning-based models; semi supervised machine learning-based models; unsupervised machine learning-based models; classification machine learning-based models; logistical regression machine learning-based models; neural network machine learning-based models; deep learning machine learning-based models; and/or any other machine learning based models discussed herein, known at the time of filing, or as developed/made available after the time of filing.

In one embodiment, once the machine learning-based physical state prediction model training data is provided to one or more machine learning-based prediction models to generate one or more trained machine learning-based physical state prediction models at 512, process flow proceeds to 514. In one embodiment, at 514, current altitude and/or motion data from one or more devices associated with a current user of an application is received.

As already discussed above, in various embodiments, a user device may be any type of device that is portable and capable of providing altitude and/or motion data, or any type of device that is portable and capable of providing raw data that can be used to calculate altitude and/or motion data, including, but not limited to, a cellular device, a handheld device, a wearable device, an implantable device, a sensor device, an accelerometer device, a motion detection device, or any other type of device currently known to those of skill in the art, or any other type of device that may be developed after the time of filing.

In one embodiment, the user device is programmed to continually collect and transmit altitude and/or motion data in real-time as the user goes about their daily activities. In one embodiment, the user device is programmed to collect and transmit altitude and/or motion data at predetermined intervals, such as once per minute, or once every 10 seconds. In some embodiments the user can determine the desired timing of data collection by entering configuration data through a user interface of the application. In some embodiments, the user may choose specific moments to collect and transmit data, or may choose when to start data collection and when to stop data collection, for example, by pushing a button on the device, toggling a switch on the device, or issuing a voice command to the device. If the device incorporates a touch screen, the user may also perform a variety of touch-based gestures to issue data collection and transmission commands to the device.

In some embodiments, the application is provided to the user on the user device, such as through a display screen of a smart phone or smart watch. In other embodiments, the user device is separate from the computing system that provides the application user interface, and the device settings may be configured through the application user interface on any type of computing system, including, but not limited to, a desktop computing system application, a mobile computing system application, a virtual reality computing system application, an application provided by an Internet of Things (IoT) device, or any combination thereof. Further, in various embodiments, the user interface may include any combination of a graphical user interface, an audio-based user interface, a touch-based user interface, or any other type of user interface currently known to those of skill in the art, or any other type of user interface that may be developed after the time of filing.

Returning briefly to FIG. 1D, in one embodiment the current device altitude and/or motion data 104 is received from user device 102 associated with user 101 by user device data acquisition module 121. In various embodiments, the current device altitude and/or motion data 104 may be stored in a portion of user database 112 that is associated with user 101 for further analysis and processing.

Returning to FIG. 5, in one embodiment, once current altitude and/or motion data from one or more devices associated with a current user of an application is received at 514, process flow proceeds to 516. In one embodiment, at 516, the current altitude and/or motion data is provided to the one or more trained machine learning-based physical state prediction models.

In one embodiment, the current altitude and/or motion data received at 514 is vectorized to generate one or more current device altitude and/or motion data vectors. The one or more current device altitude and/or motion data vectors associated with the current user are then provided as input data to the one or more trained machine learning-based physical state prediction models. The current device altitude and/or motion vector data is then processed to find a distance between the one or more current device altitude and/or motion data vectors and one or more previously labeled user device altitude and/or motion vectors, where the previously labeled user device altitude and/or motion vectors are vectors with known associated user physical state data. In one embodiment, one or more probability scores are determined based on a calculated distance between the current user device altitude and/or motion vector data and the previously labeled user device altitude and/or motion vector data. Upon determination that the one or more current user device altitude and/or motion vectors correlate to a user physical state associated with the previously labeled user device altitude and/or motion vectors, current user physical state prediction data is generated. In one embodiment, the current user physical state prediction data comprises one or more probability scores, which indicate the probability that the current user is in one or more particular physical states.

In one embodiment, the current altitude and/or motion data is first processed to generate physical activity data, such as, but not limited to, physical activity identification data, physical activity count data representing the number of times a physical activity is performed by a user in a defined timeframe, physical activity speed data representing the speed, velocity, and/or acceleration at which a physical activity is performed by a user, and/or physical activity length data representing the length of time that a user spends engaging in a physical activity. In one embodiment, the generated physical activity data is then vectorized and provided as input data to the one or more trained machine learning-based physical state prediction models.

In one embodiment, once the current altitude and/or motion data is provided to the one or more trained machine learning-based physical state prediction models at 516, process flow proceeds to 518. In one embodiment, at 518, current user physical state prediction data is received from the one or more trained machine learning-based physical state prediction models.

Returning again to FIG. 1D, as noted above, in one embodiment, the current user physical state prediction data received from the one or more trained machine learning-based physical state prediction models, which are part of trained machine learning-based mental and/or physical state prediction models 184, comprises one or more probability scores, which indicate the probability that the current user is in one or more particular physical states. The current user physical state prediction data is then aggregated with any current user mental state prediction data to generate current user mental and/or physical state prediction data 186.

Returning to FIG. 5, in one embodiment, once current user physical state prediction data is received from the one or more trained machine learning-based physical state prediction models at 518, process flow proceeds to 520. In one embodiment, at 520 one or more actions are taken, based, at least in part, on the current user physical state prediction data.

In one embodiment, upon identifying the current user's physical and/or mental state and/or identifying changes or anomalies in the current user's physical and/or mental state, one or more actions may be taken. As discussed above, in various embodiments, if an anomaly is detected in the physical and/or psychological state of the user, several types of actions may be appropriate specifically when dealing with users who are patients diagnosed with a medical condition, and the actions to be taken may be determined based on the severity of any identified anomaly. For example, if a minor anomaly is detected in the physical and/or psychological state of the user, actions might be taken such as, but not limited to: asking the user for input and/or response data; alerting the user; providing suggestions or other information to the user; making notes in, adding data to, or highlighting the user's electronic file. On the other hand, if a major anomaly is detected in the physical and/or psychological state of the user, actions might be taken such as, but not limited to: alerting one or more of the user's mental health or medical professionals; making a specialist referral; recommending support contacts to the user; prescribing additional appointments, treatments, actions, or medications; calling emergency response or intervention professionals; notifying emergency contacts, relatives, or caregivers, etc.

In various embodiments, actions that may be taken further include delivering tailored content to the user through a user interface of the application. As already noted above, the application may be provided to the user on the same user device that is used to collect the altitude and/or motion data, however the application may instead, or in addition, be provided to the user on any type of computing system. In one embodiment, a user of a digital therapeutics application is provided with a user interface, and is also provided with content-based information through the user interface. Content that may be provided includes content such as, but not limited to, information related to the user's medical history, current or potential medical care providers, medical conditions, medications, nutritional supplements, advice or suggestions regarding diet and/or exercise, or any other type of information that may be considered relevant to the user.

In addition to the types of content-based information discussed above, another type of data that may be presented to the user is user experience data. Examples of user experience data include, but are not limited to, the colors and fonts used to present the content-based information to a user, the various shapes of the graphical user interface elements, the layout or ordering of the content-based information presented to a user, and/or the sound effects, music, or other audio elements that may accompany the presentation of or interaction with the content-based information.

As noted above, the actions to be taken may be determined based on the severity of any identified anomaly. In the case of tailoring content to the user, if the anomaly is minor, then actions might be taken to make slight adjustments to the information content data and/or the user experience data that is presented to the user. On the other hand, if the anomaly is severe, then actions might be taken to make extreme adjustments to the information content data and/or the user experience data that is presented to the user. In one embodiment, adjustments to the information content data may include adjustments such as, but not limited to, providing textual content that uses gentler language, providing audio content that includes quieter, more relaxing voices, sounds, or music, or providing image/video content that is less realistic or less graphic. Adjustments to the user experience data may include adjustments such as, but not limited to, changing the colors, fonts, shapes, presentation, and/or layout of the information content data presented to the user.

In one embodiment, in addition to determining content to provide to the user based on the identification of anomalous physical activity data, the timing of notifications, alerts, or other content delivered to the user can also be determined based on the identification of anomalous physical activity data. For example, if the physical activity data indicates that a user is using the bathroom more frequently than usual, application usage reminders, therapeutic content, and other types of notifications, alerts, or content can be delivered at specific and appropriate times. The physical activity data can also be analyzed and utilized to generate or adjust one or more content delivery schedules that are tailored specifically to the user's habits and routines.

Returning again to FIG. 1D, in one embodiment, once current user mental and/or physical state prediction data 186 has been received by the one or more trained machine learning-based mental and/or physical state prediction models 184, the current user mental and/or physical state prediction data 186 is analyzed and processed by action determination module 124. In one embodiment, action determination module 124 determines one or more actions that should be taken, based on the variety of factors discussed above. Upon determination of one or more actions to be taken, action execution module 125 proceeds to take any steps necessary to execute the one or more actions. Depending on the actions determined by action determination module 124, action execution module 125 may further utilize content and user experience generation module 126, which handles the generation or modification of information content data 160 and user experience data 162 based on the current user mental and/or physical state prediction data 186. The information content data 160 and user experience data 162 may then be provided through user interface 130 to user device 102 associated with user 101 or to user computing system 134 associated with user 101 over the one or more communications networks 136.

In one embodiment, once one or more actions are taken at 520, process flow proceeds to END 522 and the process 500 for remotely identifying and monitoring anomalies in the physical state of an application user using device altitude data and machine learning models is exited to await new data and/or instructions.

The embodiments disclosed above provide an effective and efficient technical solution to the technical problem of remotely identifying and monitoring changes or anomalies in the physical and/or psychological state of application users. One specific practical application of the disclosed embodiments is that of remotely identifying and monitoring changes or anomalies in the physical and/or psychological state of patients who have been diagnosed with one or more medical conditions. In the disclosed embodiments, a patient diagnosed with one or more medical conditions is prescribed access to a digital therapeutics application, which is designed to provide guided care to the patient in a variety of ways. Through the digital therapeutics application, the patient may be provided with information, such as information relating to one or more of the patient's medical conditions, as well as current and potential medications and/or treatments. In addition, the digital therapeutics application disclosed herein collects altitude and/or motion data from one or more devices associated with the patient. The collected altitude and/or motion data is then analyzed to identify and monitor changes or anomalies in the physical and/or psychological state of the patient. Upon identification of changes or anomalies in the patient's physical and/or psychological state, one or more actions are taken to assist the patient.

Consequently, the embodiments disclosed herein are not an abstract idea, and are well-suited to a wide variety of practical applications. Further, many of the embodiments disclosed herein require processing and analysis of billions of data points and combinations of data points, and thus, the technical solution disclosed herein cannot be implemented solely by mental steps or pen and paper, is not an abstract idea, and is, in fact, directed to providing technical solutions to long-standing technical problems associated with remotely monitoring the physical and/or psychological state of application users.

Additionally, the disclosed method and system for remotely monitoring the physical and/or psychological state of application users requires a specific process comprising the aggregation and detailed analysis of large quantities of user device altitude and/or motion data, and as such, does not encompass, embody, or preclude other forms of innovation in the area of physical and/or psychological monitoring. Further, the disclosed embodiments of systems and methods for remotely monitoring the physical and/or psychological state of application users are not abstract ideas for at least several reasons.

First, effectively and efficiently monitoring the physical and/or psychological state of application users remotely is not an abstract idea because it is not merely an idea in and of itself. For example, the process cannot be performed mentally or using pen and paper, as it is not possible for the human mind to identify, process, and analyze all possible combinations of user device altitude data, user device motion data, user physical states, and user psychological states, even with pen and paper to assist the human mind and even with unlimited time.

Second, effectively and efficiently monitoring the physical and/or psychological state of application users remotely is not a fundamental economic practice (e.g., is not merely creating a contractual relationship, hedging, mitigating a settlement risk, etc.).

Third, effectively and efficiently monitoring the physical and/or psychological state of application users remotely is not merely a method of organizing human activity (e.g., managing a game of bingo). Rather, in the disclosed embodiments, the method and system for effectively and efficiently monitoring the physical and/or psychological state of application users remotely provides a tool that significantly improves the fields of medical and mental health care. Through the disclosed embodiments, patients are provided with unique and personalized remote assistance, treatment, and care. As such, the method and system disclosed herein is not an abstract idea, and also serves to integrate the ideas disclosed herein into practical applications of those ideas.

Fourth, although mathematics may be used to implement the embodiments disclosed herein, the systems and methods disclosed and claimed herein are not abstract ideas because the disclosed systems and methods are not simply a mathematical relationship/formula.

It should be noted that the language used in the specification has been principally selected for readability, clarity, and instructional purposes, and may not have been selected to delineate or circumscribe the inventive subject matter. Accordingly, the disclosure of the present invention is intended to be illustrative, but not limiting, of the scope of the invention, which is set forth in the claims below.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, or protocols. Further, the system or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic or algorithm-like descriptions and representations are the means used by those of skill in the art to most effectively and efficiently convey the substance of their work to others of skill in the art. These operations, while described functionally or logically, are understood to be implemented by computer programs or computing systems. Furthermore, it has also proven convenient at times to refer to these arrangements of operations as steps or modules or by functional names, without loss of generality.

In addition, the operations shown in the figures, or as discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computing system implemented method comprising:
   providing a user with a digital therapeutic system;
   identifying, by one or more processors of the digital therapeutic system, one or more medical conditions of the user;
   providing the user with a graphical user interface to the digital therapeutic system by which therapeutic treatment content is provided to the user, wherein the therapeutic treatment content provides treatment for the user's one or more medical conditions;
   identifying, by one or more processors of the digital therapeutic system, a physical activity performed by human beings to be monitored, wherein the number of times the physical activity is performed in a given time frame provides an indication of a status of one or more of the identified medical conditions;
   defining a change in altitude range determined to be associated with the physical activity;
   generating, by one or more processors of the digital therapeutic system, physical activity altitude data representing a correlation between the defined change in altitude range and an occurrence of the physical activity;
   generating baseline user physical activity count data representing a baseline number of occurrences of the physical activity in a defined timeframe for the user of the digital therapeutic system based on historical physical activity data associated with previous physical activities of the user;

collecting, by one or more processors of the digital therapeutic system, objectively measured current user altitude data from one or more remote monitoring devices associated with the user of the digital therapeutic system;

analyzing, by one or more processors of the digital therapeutic system, the current user altitude data and the physical activity altitude data to identify one or more current occurrences of the user engaging in the physical activity;

based on the current user altitude data, generating current user physical activity count data representing the current number of times the physical activity is performed by the user in the defined timeframe;

comparing the current user physical activity count data with the baseline user physical activity count data;

if the current user physical activity count data differs from the baseline user physical activity count data by a threshold amount, automatically determining, by one or more processors of the digital therapeutic system, a current status of the one or more medical conditions of the user of the digital therapeutics system;

based on the determined current status of the one or more medical conditions of the user, dynamically modifying, by one or more processors of the digital therapeutic system, the therapeutic treatment content provided to the user through the graphical user interface of the digital therapeutic system, wherein the modified therapeutic treatment content provides treatment for the user's one or more medical conditions; and providing the modified therapeutic treatment content to the user through the graphical user interface of the digital therapeutic system.

2. The computing system implemented method of claim 1 wherein the remote monitoring device associated with the user is a device selected from the group of devices containing:
cellular devices;
handheld devices;
wearable devices;
implantable devices;
sensor devices;
accelerometer devices; and
motion detection devices.

3. The computing system implemented method of claim 1 wherein the physical activity performed by human beings includes one or more of:
standing;
sitting;
exercising;
urinating;
defecating;
bathing;
lying down; and
sleeping.

4. The computing system implemented method of claim 1 wherein, based on the determined current status of the one or more medical conditions of the user, additional actions are taken, including one or more of:
verifying the identity of the user;
providing personalized content to the user through the user interface of the digital therapeutic system;
requesting information from the user through the user interface of the digital therapeutic system;
updating a profile associated with the user;
contacting the user directly;
contacting a third party on the user's behalf;
adding a note to the user's file for review by a third party; and
flagging the user's file for attention by a third party.

5. The computing system implemented method of claim 4 wherein providing personalized content to the user includes:
generating personalized content based on the number of times the physical activity is performed by the user in the defined timeframe;
determining a content schedule for providing the personalized content to the user based on the number of times the physical activity is performed by the user in the defined timeframe; and
providing the user with the personalized content at a frequency determined by the content schedule.

6. The computing system implemented method of claim 5 wherein generating personalized content based on the number of times the physical activity is performed by the user in the defined timeframe includes one or more of:
determining one or more current medical conditions of the user based on the number of times the physical activity is performed by the user in the defined timeframe;
determining the current physical state of the user based on the number of times the physical activity is performed by the user in the defined timeframe;
determining the current mental state of the user based on the number of times the physical activity is performed by the user in the defined timeframe;
predicting one or more future medical conditions of the user based on the number of times the physical activity is performed by the user in the defined timeframe;
predicting a future physical state of the user based on the number of times the physical activity is performed by the user in the defined timeframe;
predicting a future mental state of the user based on the number of times the physical activity is performed by the user in the defined timeframe; and
predicting the number of times the physical activity will be performed by the user in a future timeframe.

7. The computing system implemented method of claim 5 wherein the personalized content that is generated based on the number of times the physical activity is performed by the user in the defined timeframe includes one or more of:
information related to the identity of the user;
information related to a medication of the user;
information related to a current medical condition of the user;
information related to a current physical state of the user;
information related to a current mental state of the user;
information related to a predicted future medical condition of the user;
information related to a predicted future physical state of the user; and
information related to a predicted future mental state of the user.

8. The computing system implemented method of claim 4 wherein the third party is one or more of:
a medical professional associated with the user;
an emergency contact associated with the user; and
a relative of the user.

9. A computing system implemented method comprising:
providing a user with a digital therapeutic system;
identifying, by one or more processors of the digital therapeutic system, one or more medical conditions of the user;

providing the user with a graphical user interface to the digital therapeutic system by which therapeutic treatment content is provided to the user, wherein the therapeutic treatment content provides treatment for the user's one or more medical conditions;

identifying, by one or more processors of the digital therapeutic system, a physical activity performed by human beings to be monitored, wherein the number of times the physical activity is performed in a given time frame provides an indication of a status of one or more of the identified medical conditions;

defining a change in motion range determined to be associated with the physical activity;

generating, by one or more processors of the digital therapeutic system, physical activity motion data representing a correlation between the defined change in motion range and an occurrence of the physical activity;

generating baseline user physical activity count data representing a baseline number of occurrences of the physical activity in a defined timeframe for the user of the digital therapeutic system based on historical physical activity data associated with previous physical activities of the user;

collecting, by one or more processors of the digital therapeutic system, objectively measured current user motion data from one or more remote monitoring devices associated with the user of the digital therapeutic system;

analyzing, by one or more processors of the digital therapeutic system, the current user motion data and the physical activity motion data to identify one or more current occurrences of the user engaging in the physical activity;

based on the current user motion data, generating current user physical activity count data representing the current number of times the physical activity is performed by the user in the defined timeframe;

comparing the current user physical activity count data with the baseline user physical activity count data;

if the current user physical activity count data differs from the baseline user physical activity count data by a threshold amount, automatically determining, by one or more processors of the digital therapeutic system, a current status of the one or more medical conditions of the user of the digital therapeutics system;

based on the determined current status of the one or more medical conditions of the user, dynamically modifying, by one or more processors of the digital therapeutic system, the therapeutic treatment content provided to the user through the graphical user interface of the digital therapeutic system, wherein the modified therapeutic treatment content provides treatment for the user's one or more medical conditions; and providing the modified therapeutic treatment content to the user through the graphical user interface of the digital therapeutic system.

10. The computing system implemented method of claim 9 wherein the remote monitoring device associated with the user is a device selected from the group of devices containing:
cellular devices;
handheld devices;
wearable devices;
implantable devices;
sensor devices;
accelerometer devices; and
motion detection devices.

11. The computing system implemented method of claim 9 wherein the physical activity performed by human beings includes one or more of:
standing;
walking;
running;
exercising;
pacing;
sitting;
eating;
urinating;
defecating;
bathing;
lying down; and
sleeping.

12. The computing system implemented method of claim 9 wherein, based on the determined current status of the one or more medical conditions of the user, additional actions are taken, including one or more of:
verifying the identity of the user;
providing personalized content to the user through the user interface of the digital therapeutic system;
requesting information from the user through the user interface of the digital therapeutic system;
updating a profile associated with the user;
contacting the user directly;
contacting a third party on the user's behalf;
adding a note to the user's file for review by a third party; and
flagging the user's file for attention by a third party.

13. The computing system implemented method of claim 12 wherein providing personalized content to the user includes:
generating personalized content based on the number of times the physical activity is performed by the user in the defined timeframe;
determining a content schedule for providing the personalized content to the user based on the number of times the physical activity is performed by the user in the defined timeframe; and
providing the user with the personalized content at a frequency determined by the content schedule.

14. The computing system implemented method of claim 13 wherein generating personalized content based on the number of times the physical activity is performed by the user in the defined timeframe includes one or more of:
determining one or more current medical conditions of the user based on the number of times the physical activity is performed by the user in the defined timeframe;
determining the current physical state of the user based on the number of times the physical activity is performed by the user in the defined timeframe;
determining the current mental state of the user based on the number of times the physical activity is performed by the user in the defined timeframe;
predicting one or more future medical conditions of the user based on the number of times the physical activity is performed by the user in the defined timeframe;
predicting a future physical state of the user based on the number of times the physical activity is performed by the user in the defined timeframe;
predicting a future mental state of the user based on the number of times the physical activity is performed by the user in the defined timeframe; and
predicting the number of times the physical activity will be performed by the user in a future timeframe.

15. The computing system implemented method of claim 13 wherein the personalized content that is generated based on the number of times the physical activity is performed by the user in the defined timeframe includes one or more of:
information related to the identity of the user;
information related to a medication of the user;
information related to a current medical condition of the user;
information related to a current physical state of the user;
information related to a current mental state of the user;
information related to a predicted future medical condition of the user;
information related to a predicted future physical state of the user; and
information related to a predicted future mental state of the user.

16. The computing system implemented method of claim 12 wherein the third party is one or more of:
a medical professional associated with the user;
an emergency contact associated with the user; and
a relative of the user.

17. A system comprising:
a digital therapeutic system;
a graphical user interface to the digital therapeutic system by which therapeutic treatment content is provided to a user, wherein the therapeutic treatment content provides treatment for one or more medical conditions of the user;
one or more databases, the one or more databases including data identifying a physical activity performed by human beings to be monitored, data defining a change in altitude range determined to be associated with the physical activity, physical activity altitude data representing a correlation between the defined change in altitude range and an occurrence of the physical activity, and baseline user physical activity count data representing a baseline number of occurrences of the physical activity in a defined timeframe for the user of the digital therapeutic system;
one or more remote monitoring devices associated with the user of the digital therapeutic system;
one or more processors; and
one or more physical memories, the one or more physical memories having stored therein data representing instructions which when processed by the one or more processors perform a process, the process comprising:
collecting objectively measured current user altitude data from the one or more remote monitoring devices associated with the user of the digital therapeutic system;
analyzing the current user altitude data and the physical activity altitude data to identify one or more current occurrences of the user engaging in the physical activity;
based on the current user altitude data, generating current user physical activity count data representing the current number of times the physical activity is performed by the user in the defined timeframe;
comparing the current user physical activity count data with the baseline user physical activity count data;
if the current user physical activity count data differs from the baseline user physical activity count data by a threshold amount, automatically determining a current status of the one or more medical conditions of the user of the digital therapeutics system;
based on the determined current status of the one or more medical conditions of the user, dynamically modifying the therapeutic treatment content provided to the user through the graphical user interface of the digital therapeutic system, wherein the modified therapeutic treatment content provides treatment for one or more medical conditions of the user; and
providing the modified therapeutic treatment content to the user through the graphical user interface of the digital therapeutic system.

18. The system of claim 17 wherein the physical activity performed by human beings includes one or more of:
standing;
sitting;
exercising;
urinating;
defecating;
bathing;
lying down; and
sleeping.

19. The system of claim 17 wherein, based on the determined current status of the one more medical conditions of the user, additional actions are taken, including one or more of:
verifying the identity of the user;
providing personalized content to the user through the user interface of the digital therapeutic system;
requesting information from the user through the user interface of the digital therapeutic system;
updating a profile associated with the user;
contacting the user directly;
contacting a third party on the user's behalf;
adding a note to the user's file for review by a third party; and
flagging the user's file for attention by a third party.

20. A system comprising:
a digital therapeutic system;
a graphical user interface to the digital therapeutic system by which therapeutic treatment content is provided to a user, wherein the therapeutic treatment content provides treatment for one or more medical conditions of the user;
one or more databases, the one or more databases including data identifying a physical activity performed by human beings to be monitored, data defining a change in motion range determined to be associated with the physical activity, physical activity motion data representing a correlation between the defined change in motion range and an occurrence of the physical activity, and baseline user physical activity count data representing a baseline number of occurrences of the physical activity in the defined timeframe for the user of the digital therapeutic system;
one or more remote monitoring devices associated with the user of the digital therapeutic system;
one or more processors; and
one or more physical memories, the one or more physical memories having stored therein data representing instructions which when processed by the one or more processors perform a process, the process comprising:
collecting objectively measured current user motion data from the one or more remote monitoring devices associated with the user of the digital therapeutic system;
analyzing the current user motion data and the physical activity motion data to identify one or more current occurrences of the user engaging in the physical activity;

based on the current user motion data, generating current user physical activity count data representing the current number of times the physical activity is performed by the user in the defined timeframe;

comparing the current user physical activity count data with the baseline user physical activity count data;

if the current user physical activity count data differs from the baseline user physical activity count data by a threshold amount, automatically determining a current status of the one or more medical conditions of the user of the digital therapeutics system;

based on the determined current status of the one or more medical conditions of the user, dynamically modifying the therapeutic treatment content provided to the user through the graphical user interface of the digital therapeutic system, wherein the modified therapeutic treatment content provides treatment for one or more medical conditions of the user; and providing the modified therapeutic treatment content to the user through the graphical user interface of the digital therapeutic system.

21. The system of claim 20 wherein the physical activity performed by human beings includes one or more of:
standing;
walking;
running;
exercising;
pacing;
sitting;
eating;
urinating;
defecating;
bathing;
lying down; and
sleeping.

22. The computing system implemented method of claim 20 wherein, based on the determined current status of the one or more medical conditions of the user, additional actions are taken, including one or more of:
verifying the identity of the user;
providing personalized content to the user through the user interface of the digital therapeutic system;
requesting information from the user through the user interface of the digital therapeutic system;
updating a profile associated with the user;
contacting the user directly;
contacting a third party on the user's behalf;
adding a note to the user's file for review by a third party; and
flagging the user's file for attention by a third party.

* * * * *